(12) United States Patent
Chow et al.

(10) Patent No.: US 7,884,244 B2
(45) Date of Patent: Feb. 8, 2011

(54) THERAPEUTIC FLUOROETHYLCYANO GUANIDINES

(75) Inventors: Ken Chow, Newport Coast, CA (US); Wenkui K. Fang, Irvine, CA (US); Evelyn G. Corpuz, Irvine, CA (US); Daniel W. Gil, Corona Del Mar, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 195 days.

(21) Appl. No.: 12/058,037

(22) Filed: Mar. 28, 2008

(65) Prior Publication Data

US 2008/0255230 A1 Oct. 16, 2008

Related U.S. Application Data

(60) Provisional application No. 60/911,478, filed on Apr. 12, 2007.

(51) Int. Cl.
*C07C 277/00* (2006.01)

(52) U.S. Cl. ........... 564/230; 564/238; 564/239; 514/391; 514/634; 558/391; 549/467

(58) Field of Classification Search .......... None
See application file for complete search history.

(56) References Cited

U.S. PATENT DOCUMENTS

| | | | | |
|---|---|---|---|---|
| 6,787,569 | B1 * | 9/2004 | Goldin et al. ........ | 514/634 |
| 6,916,813 | B2 * | 7/2005 | Atwal et al. ........ | 514/235.8 |

FOREIGN PATENT DOCUMENTS

WO WO 2006125116 * 11/2006

OTHER PUBLICATIONS

Rossiter et al, Journal of Medicinal chemistry, 2005, 48(14), 4670-4678.*

Berrier, C.; Gesson, J. P.; Jacquesy, J. C.; Renoux, A. *Tetrahedron* 1984, 40, 4973-4980.
Baddar et al. *J. Chem. Soc.* 1959, 1027-1029.
Bunnett, J.F.; Skorcz, J.A. *J. Org. Chem.* 1962, 27, 3836-3843.
Burnham, J.W. et al. *J. Org. Chem.* 1974, 39, 1416-1420.
Cope, A. C.; Liss, T. A.; Smith, D. S. *J. Am. Chem. Soc.* 1957, 79, 240-243.
Eli Lilly and Co. Indianapolis, Ind.(V.St.A), DE 2812578, 1978, Chem.Abstr. 90, 54730.
Faller, P. *Bull. Soc. Chim. Fr.* 1966, 3618-3625.
Kuiban et al. J.Gen.Chem.Ussr (Engl.Transl.) 1964, 34, 1592; *Zh. Obshch. Khim.* 1964, 34, 1581.
Musso, David L.; Cochran, Felicia R.; Kelley, James L.; McLean, Ed W.; Selph, Jeffrey L.; Rigdon, Greg C.; Orr, G. Faye; Davis, Ronda G.; Cooper, Barrett R.; Styles, Virgil L.; Thompson, James B.; Hall, William R. *J. Med. Chem.* 2003, 46, 399-408.
Nakamura, Y.; O-kawa, K.; Minami, S.; Ogawa, T.; Tobita, S.; Nishimura, J. *J. Org. Chem.* 2002, 67, 1247-1252.
Stipanovic, B.; Pines, H. *J. Org. Chem.* 1969, 34, 2106-2113.
Staab, Heinz A.; Nikolic, Susanne; Krieger, Claus *Eur. J. Org. Chem.* 1999, 6, 1459-1470.
Tasker, Andrew S.; Sorensen, Bryan K.; Jae, Hwan-Soo; Winn, Martin; Geldern, Thomas W. von; et al. *J. Med. Chem.* 1997, 40, 322-330.
Zhang, Jin-Tao; Dai, Wei; Harvey, Ronald G. *J. Org. Chem.* 1998, 63, 8125-8132.
Zhang, Xiaoyan; Angeles, Joseph E. De Los; He, Mei-Ying; Dalton, James T.; Shams, Gamal; et al. J. Med. Chem. 1997, 40, 3014-3024.

* cited by examiner

*Primary Examiner*—Sudhakar Katakam
(74) *Attorney, Agent, or Firm*—Doina G. Ene; John E. Wurst; Kevin J. Forrestal

(57) ABSTRACT

Disclosed herein is compound having a formula

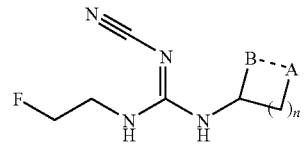

as described herein. Therapeutic methods, compositions, and medicaments related thereto are also disclosed.

13 Claims, No Drawings

THERAPEUTIC FLUOROETHYLCYANO GUANIDINES

CROSS REFERENCE TO RELATED APPLICATIONS

This application claims the benefit of U.S. Provisional Application Ser. No. 60/911,478 filed Apr. 12, 2007, which is hereby incorporated by reference in its entirety.

DESCRIPTION OF THE INVENTION

There is an ongoing need for compounds that are useful for treating pain.

The compounds disclosed herein are useful to treat chronic pain, allodynia, muscle spasticity, diarrhea, neuropathic pain, and/or visceral pain.

These compounds are generally described by the formula

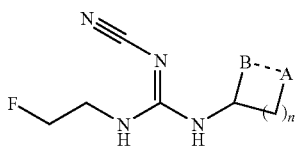

wherein a dashed line indicates the presence or absence of a bond;
n is 0 or 1;
A is substituted or unsubstituted phenyl;
B is alkyl having 1, 2, 3, or 4 carbon atoms; or
B is H or substituted or unsubstituted phenyl and the dashed line is not a covalent bond.

Unless otherwise indicated, reference to a compound should be construed broadly to include pharmaceutically acceptable salts, and tautomers of the depicted structure. For example, the structures herein are intended to include, but are not limited to, the tautomeric forms shown below.

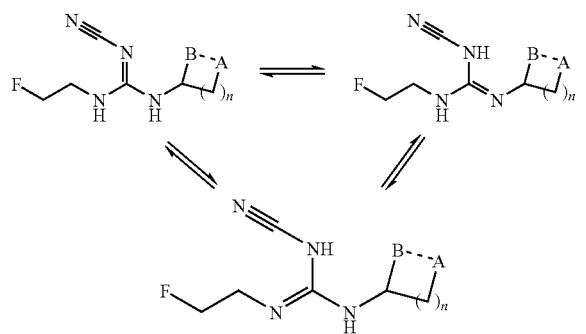

A "pharmaceutically acceptable salt" is any salt that retains the activity of the parent compound and does not additional unacceptable deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Unless stereochemistry is explicitly depicted, a structure is intended to include every possible stereoisomer, both pure or in any possible mixture.

Since a dashed line indicates the presence or absence of a bond, compounds according to the structures below are possible.

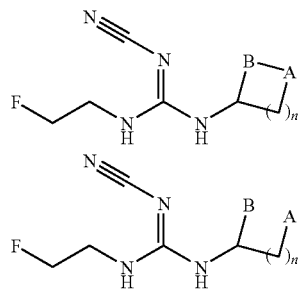

Because n is 0 or 1, compounds according to any of the structures below are possible.

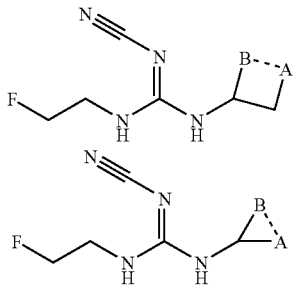

A is substituted or unsubstituted phenyl.

Substituted phenyl may have 1, 2, 3, 4, or 5 substituents. The substituents have from 0 to 6 carbon atoms, from 0 to 3 oxygen atoms, from 0 to 2 sulfur atoms, from 0 to 1 nitrogen atoms, from 0 to 3 fluorine atoms, 0 or 1 chlorine atom, 0 or 1 bromine atom, and 0 or 1 iodine atoms. Two substituents may form a ring such that if the dashed line in the general structure is not a covalent bond, phenyl is part of a bicyclic system, or if the dashed line in the general structure is a covalent bond, phenyl is part of a tricyclic ring system.

For example, the core structures shown below are possible, wherein the ring system may have additional substituents subject to the constraints defined herein.

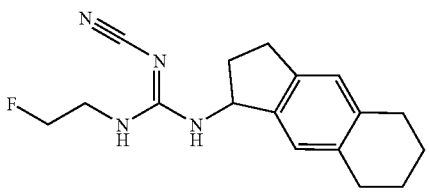

-continued

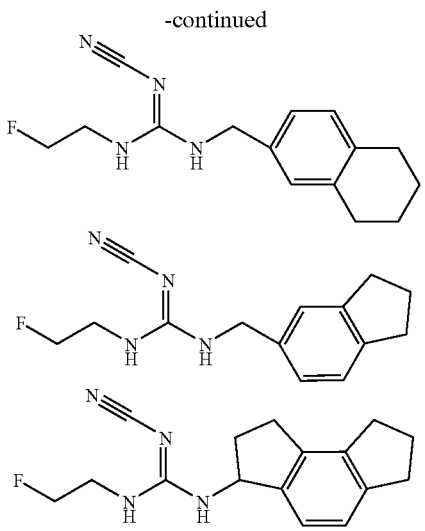

Examples of substituents include, but are not limited to:

Hydrocarbyl having from 1 to 6 carbon atoms including, but not limited to:
  a. alkyl having from 1 to 6 carbon atoms, including, but not limited to:
     linear alkyl, e.g. methyl, ethyl, n-propyl, n-butyl, n-pentyl, n-hexyl, etc.,
     branched alkyl, e.g. iso-propyl, t-butyl and other branched butyl isomers, branched pentyl isomers, etc.,
     cycloalkyl, e.g. cyclopropyl, cyclobutyl, cyclopentyl, cyclohexyl, etc.,
     combinations of linear, branched, and/or cycloalkyl;
  b. alkenyl having from 1 to 6 carbon atoms, e.g. hydrocarbyl having 1 or more double bonds, including linear, branched, or cycloalkenyl
  c. alkynyl having from 1 to 6 carbon atoms, e.g. hydrocarbyl having 1 or more triple bonds, including linear, branched, or cycloalkenyl;
  d. combinations of alkyl, alkenyl, and/or akynyl alkyl-CN having from 1 to 6 carbon atoms; hydroxyalkyl, i.e. alkyl-OH, such as hydroxymethyl, hydroxyethyl, and the like;

ether substituents, including O-alkyl, alkyl-O-alkyl, and the like, having from 1 to 6 carbon atoms;

thioether substituents, including S-alkyl, alkyl-5-alkyl, and the like, having from 1 to 6 carbon atoms;

amine substituents, including $NH_2$, NH-alkyl, N-alkyl$^1$alkyl$^2$ (i.e., alkyl$^1$ and alkyl$^2$ are the same or different, both attached to N), alkyl-$NH_2$, alkyl-NH-alkyl, alkyl-N-alkyl$^1$alkyl$^2$, and the like;

ester substituents, including $CO_2$-alkyl, $CO_2$-phenyl, etc., having from 1 to 6 carbon atoms;

other carbonyl substituents, including aldehydes; ketones, such as acyl (i.e.

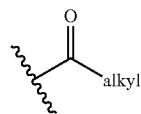

), and the like;

phenyl, provided that the ring and any substituents remain with the constraints defined herein;

fluorocarbons or hydrofluorocarbons such as $CF_3$, $CH_2CF_3$, etc.; and

CN;

combinations of the above are also possible, subject to the constraints defined;

Alternatively, a substituent may be F, Cl, Br, or I.

Substituents must be sufficiently stable to be stored in a bottle at room temperature under a normal atmosphere for at least 12 hours, or stable enough to be useful for any purpose disclosed herein.

If a substituent is a salt, for example of a carboxylic acid or an amine, the counter-ion of said salt, i.e. the ion that is not covalently bonded to the remainder of the molecule is not counted for the purposes of the number of heavy atoms in a substituent. Thus, for example, the salt —$CO_2^-Na^+$ is a stable substituent consisting of 3 heavy atoms, i.e. sodium is not counted. In another example, the salt —$NH(Me)_2^+Cl^-$ is a stable substituent consisting of 3 heavy atoms, i.e. chlorine is not counted.

B is alkyl having 1, 2, 3, or 4 carbon atoms; or B is H or substituted or unsubstituted phenyl, wherein the dashed line is not a covalent bond. In other words B can be:

$C_{1-4}$ alkyl, e.g. methyl, ethyl, propyl isomers, butyl isomers, etc., including linear, branched, and cyclic alkyl (e.g. cyclopropyl, cyclobutyl) or a combination of linear, branched, and/or cyclic alkyl; or B can be H, so that a compound has the formula below.

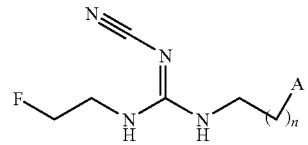

Or B can be substituted or unsubstituted phenyl and the dashed line is not a covalent bond. For example, compounds according the structure below are possible, wherein $R^a$ and $R^b$ are independently H, or are substituents as defined herein.

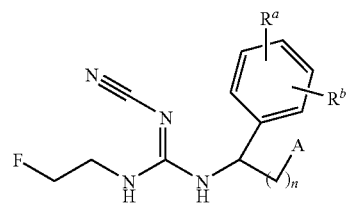

In one embodiment, A is phenyl substituted with 0, 1, 2, 3, or 4 substituents, wherein the substituents are independently alkyl having from 1 to 4 carbon atoms or a halogen.

In another embodiment, the substituents of A are independently methyl, ethyl, F, Cl, or Br.

In another embodiment, A is unsubstituted phenyl.

Another embodiment is a compound having a formula

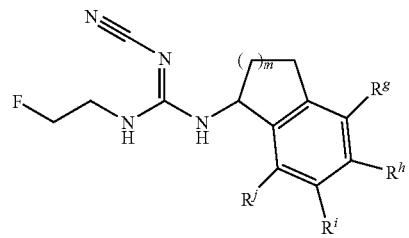

wherein m is 0 or 1; and $R^g$, $R^h$, $R^i$, and $R^j$ are independently H, alkyl having from 1 to 6 carbon atoms, halogen, CN, $CH_2CN$, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

Another embodiment is a compound having a formula

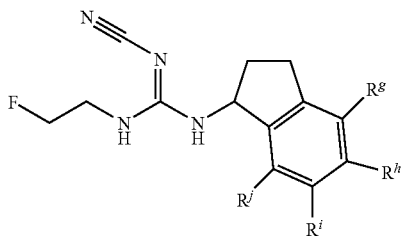

wherein $R^g$, $R^h$, $R^i$, and $R^j$ are independently H, alkyl having from 1 to 6 carbon atoms, halogen, CN, $CH_2CN$, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

Another embodiment is a compound having a formula

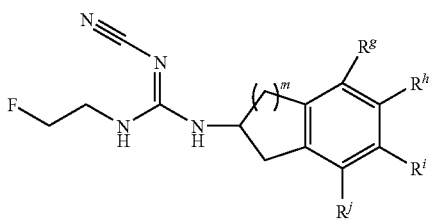

wherein m is 0 or 1; and $R^g$, $R^h$, $R^i$, and $R^j$ are independently H, alkyl having from 1 to 6 carbon atoms, halogen, CN, $CH_2CN$, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

Another embodiment is a compound having a formula

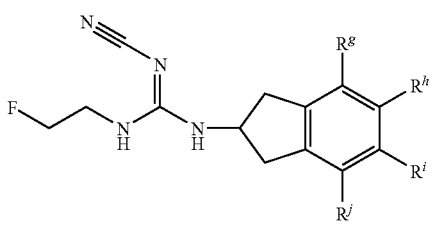

wherein $R^g$, $R^h$, $R^i$, and $R^j$ are independently H, alkyl having from 1 to 6 carbon atoms, halogen, CN, $CH_2CN$, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

Another embodiment is a compound having a formula

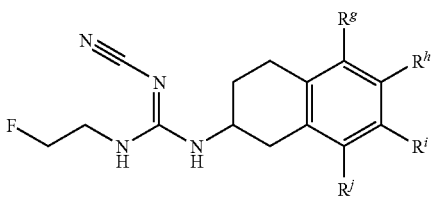

wherein $R^g$, $R^h$, $R^i$, and $R^j$ are independently H, alkyl having from 1 to 6 carbon atoms, halogen, CN, $CH_2CN$, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

Another embodiment is a compound having a formula

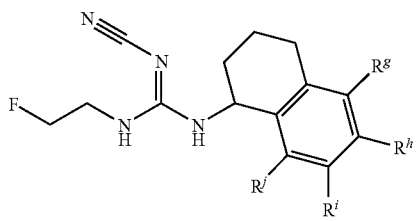

wherein $R^g$, $R^h$, $R^i$, and $R^j$ are independently H, alkyl having from 1 to 6 carbon atoms, halogen, CN, $CH_2CN$, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

Another embodiment is a compound having a formula

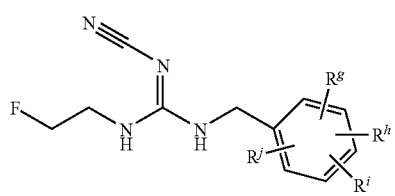

wherein $R^g$, $R^h$, $R^i$, and $R^j$ are independently H, alkyl having from 1 to 6 carbon atoms, halogen, CN, $CH_2CN$, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

Another embodiment is a compound having a formula

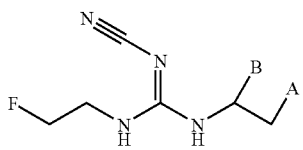

wherein A is substituted or unsubstituted phenyl; and
B is substituted or unsubstituted phenyl.

Hypothetical examples of useful embodiments are depicted below.
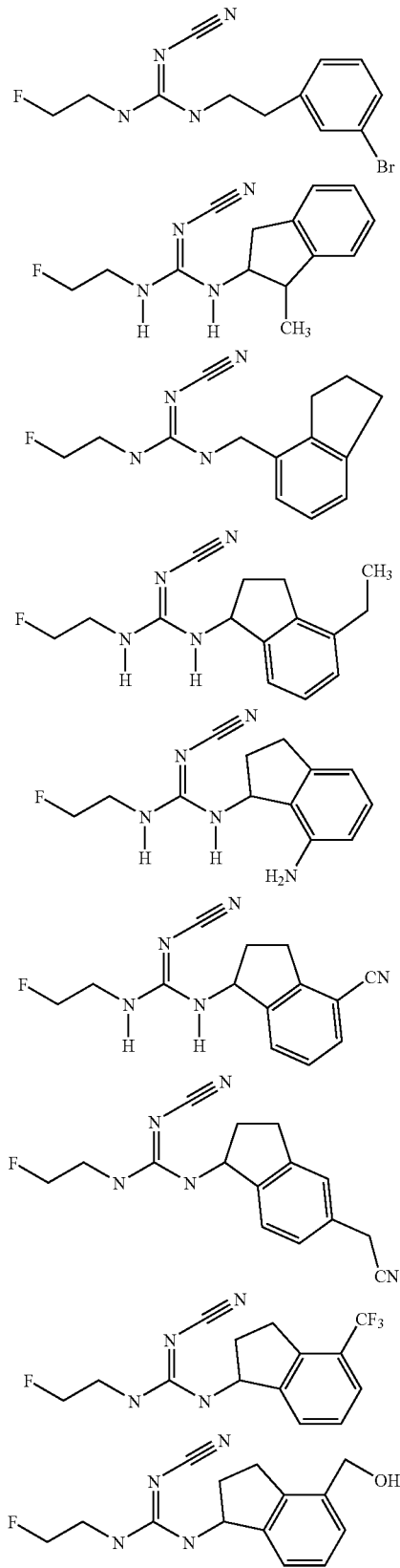
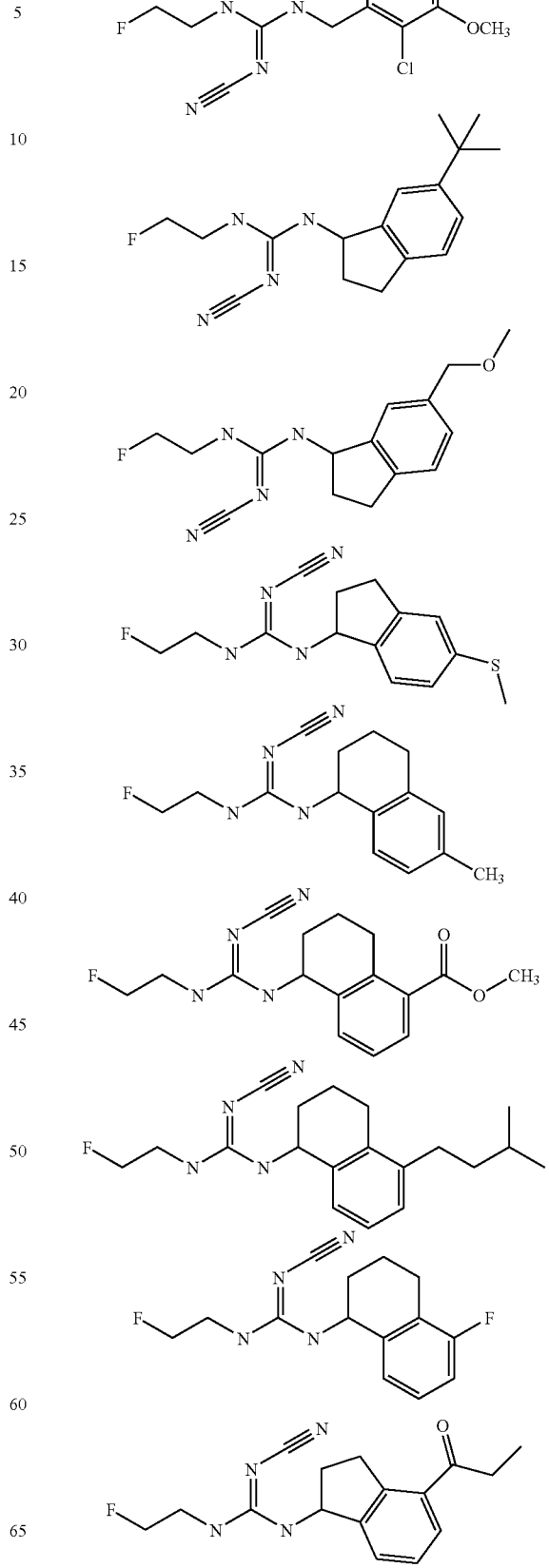

-continued

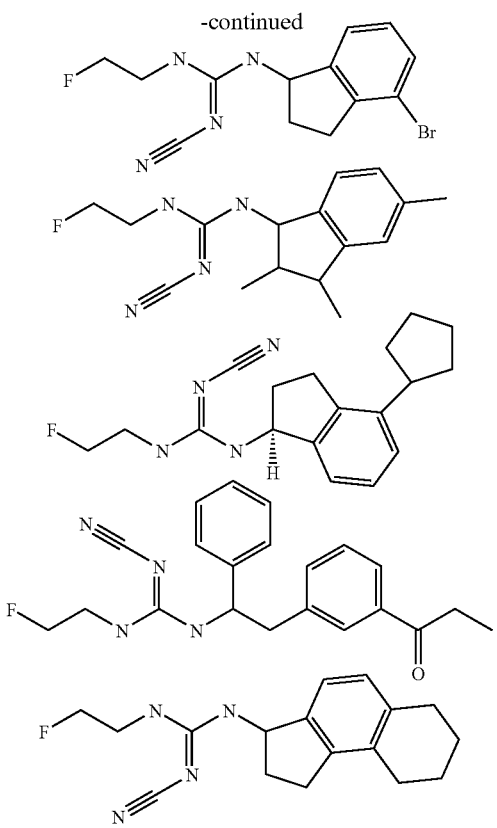

For the purposes of this disclosure, "treat," "treating," or "treatment" refer to the use of a compound, composition, therapeutically active agent, or drug in the diagnosis, cure, mitigation, treatment, prevention of disease or other undesirable condition.

These compounds may be formulated into solid, liquid, or other types of dosage forms using methods known in the art. Both formulation of dosage forms and determination of a therapeutically effective dose can be readily made by a person of ordinary skill using routine methods.

BIOLOGICAL DATA

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as □-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-□-galactosidase (5-10 µg), receptor (1-2 µg) and G protein (1-2 µg). 40 µg salmon sperm DNA may also be included in the transfection mixture. Fresh media is added on the following day and 1-2 days later, cells are harvested and frozen in 50 assay aliquots. Cells are thawed and 100 µl added to 100 µl aliquots of various concentrations of drugs in triplicate in 96-well dishes. Incubations continue 72-96 hr at 37° C. After washing with phosphate-buffered saline, □-galactosidase enzyme activity is determined by adding 200 µl of the chromogenic substrate (consisting of 3.5 mM o-nitrophenyl-□-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors. The EC$_{50}$ is the concentration at which the drug effect is half of its maximal effect.

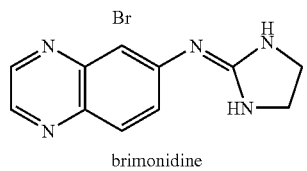

brimonidine

The results of the RSAT assay with several exemplary compounds of the invention are disclosed in Table 1 above together with the chemical formulas of these exemplary compounds. EC$_{50}$ values are nanomolar. NA stands for "not active" at concentrations less than 10 micromolar. IA stands for "intrinsic activity."

TABLE 1

| | Alpha 2A | | Alpha 2B | | Alpha 2C | |
|---|---|---|---|---|---|---|
| | EC$_{50}$ | IA | EC$_{50}$ | IA | EC$_{50}$ | IA |
| | not active | | 1450 | 0.82 | 2640 | 0.32 |

TABLE 1-continued

| | Alpha 2A | | Alpha 2B | | Alpha 2C | |
|---|---|---|---|---|---|---|
| | EC$_{50}$ | IA | EC$_{50}$ | IA | EC$_{50}$ | IA |
| [structure: F-ethyl-N-cyanoguanidine-2-indanyl] | not active | | 783 | 0.35 | not active | |
| [structure: F-ethyl-N-cyanoguanidine-CH2-dihydrobenzofuran] | not active | | 341 | 0.87 | 358 | 0.58 |
| [structure: F-ethyl-N-cyanoguanidine-1-indanyl-4-CH3] | not active | | 73.9 | 0.95 | 914 | 0.51 |
| [structure: F-ethyl-N-cyanoguanidine-1-indanyl] | not active | | 417 | 0.47 | 1780 | 0.33 |
| [structure: F-ethyl-N-cyanoguanidine-1-indanyl-4-Br] | not active | | 2570 | 0.74 | not active | |
| [structure: F-ethyl-N-cyanoguanidine-1-indanyl Chiral] | not active | | 176 | 0.92 | not active | |
| [structure: F-ethyl-N-cyanoguanidine-1-indanyl-4-Cl] | not active | | 988 | 0.3 | not active | |
| [structure: F-ethyl-N-cyanoguanidine-1-indanyl-4-F] | not active | | 282 | 0.36 | not active | |

TABLE 1-continued
| | Alpha 2A | | Alpha 2B | | Alpha 2C | |
|---|---|---|---|---|---|---|
| | $EC_{50}$ | IA | $EC_{50}$ | IA | $EC_{50}$ | IA |
| 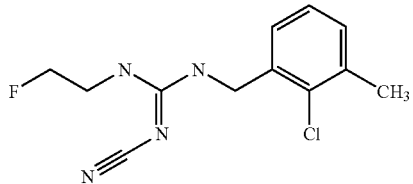 | not active | | 78.9 | 0.93 | 472 | 0.84 |
| 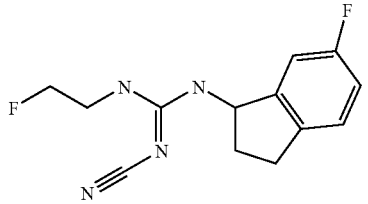 | not active | | 167 | 0.42 | 376 | 0.4 |
| 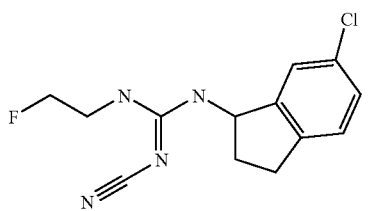 | not active | | 232 | 0.31 | 946 | 0.36 |
| 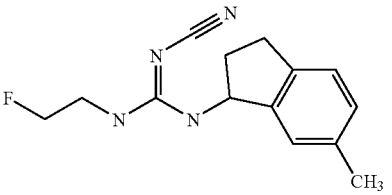 | not active | | 518 | 0.34 | not active | |
| 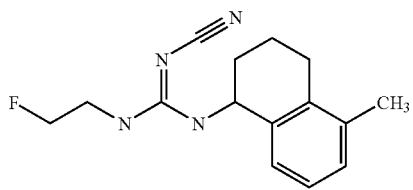 | not active | | 94.3 | 1.06 | 1480 | 0.41 |
| 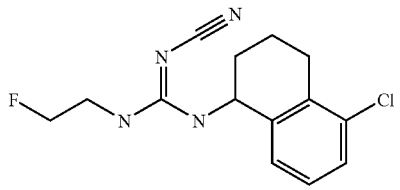 | not active | | 296 | 0.37 | not active | |
| 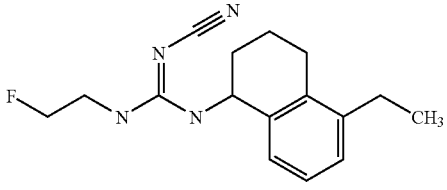 | not active | | high | 0.35 | not active | |

TABLE 1-continued
|  | Alpha 2A | | Alpha 2B | | Alpha 2C | |
| --- | --- | --- | --- | --- | --- | --- |
|  | EC$_{50}$ | IA | EC$_{50}$ | IA | EC$_{50}$ | IA |
| 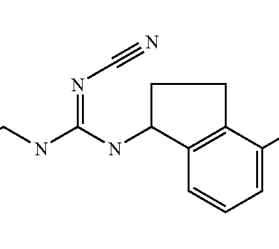 | not active |  | 231 | 0.69 | 1970 | 0.42 |
| 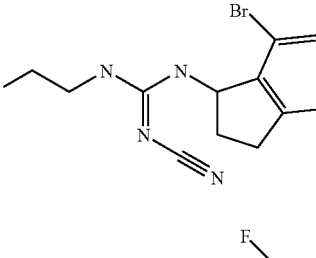 | not active |  | 1040 | 0.59 | not active |  |
| 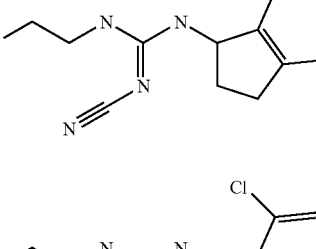 | not active |  | 941 | 0.85 | not active |  |
| 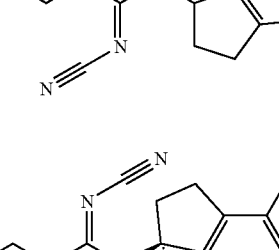 | not active |  | 475 | 0.65 | not active |  |
| 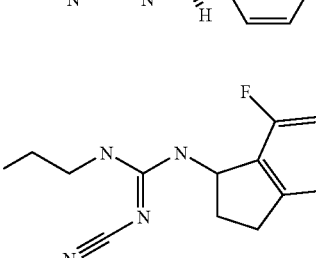 | not active |  | 642 | 0.7 | not active |  |
| Chiral  | 759 | 0.35 | 60.1 | 1.09 | 1530 | 0.46 |
|  | not active |  | 560 | 0.5 | not active |  |

TABLE 1-continued

| | Alpha 2A | | Alpha 2B | | Alpha 2C | |
|---|---|---|---|---|---|---|
| | $EC_{50}$ | IA | $EC_{50}$ | IA | $EC_{50}$ | IA |
| | not active | | 98.6 | 0.73 | not active | |

Synthetic Methods

General Procedure A for the Synthesis of 1-(2-Fluoroethyl)-3-Aryl Cyanoguanidines

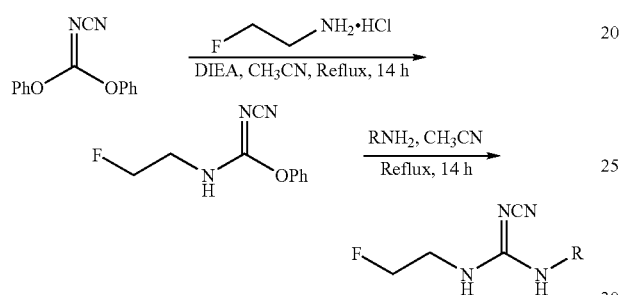

Fluoroethyl amine hydrochloride (5.50 g, 90% purity, 49.75 mmol) was added to a solution of diphenyl cyanocarbonimidate (11.84 g, 49.70 mmol) in $CH_3CN$, followed by addition of diisopropylethyl amine (17.30 mL, 99.32 mmol). After stirring for 14 hours, the reaction mixture was concentrated and the residue was taken up in EtOAc. The organic layer was washed sequentially with $H_2O$ (3×75 mL) and aq 2N KOH (3×100 mL), then concentrated to give a viscous oil, which was solidified upon standing at room temperature. Recrystallization from ether gave the desired 1-(2-fluoroethyl)-2-phenyl-3-cyanoisourea intermediate. A portion of this intermediate was mixed with an appropriate amine in $CH_3CN$. The resulting reaction mixture was refluxed for 14 hours. After cooling to room temperature, the mixture was diluted with EtOAc and the resulting organic phase was washed with $H_2O$ (3×75 mL) and then concentrated. The residue was purified by column chromatography using hex: EtOAc (2:3) as eluant to give a semi-pure product. Recrystallization from EtOAc afforded the final pure cyanoguanidine.

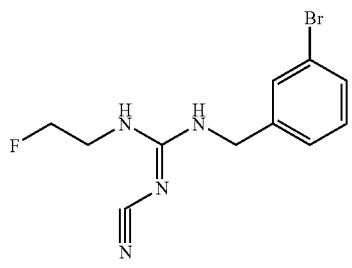

Synthesis of 1-(3-Bromo-benzyl)-3-(2-fluoro-ethyl)-cyanoguanidine

The title compound was generated from the commercially available 3-bromobenzylamine according to the general procedure A described above.

1-(3-Bromo-benzyl)-3-(2-fluoro-ethyl)-cyanoguanidine: The title compound was obtained from 3-bromo-benzylamine (1.70 g, 9.00 mmol) and 1-(2-fluoro-ethyl)-2-phenyl-3-cyanoisourea (1.00 g, 4.83 mmol) in $CH_3CN$ according to general procedure A described above. Spectroscopic data: $^1H$ NMR (300 MHz, DMSO-$d_6$) ☐ 3.4 (q, J=5.3 Hz, 1H), 3.5 (q, J=5.3 Hz, 1H), 4.30-4.41 (m, 3H), 4.5 (t, J=5.0 Hz, 1H), 7.24-7.34 (m, 3H), 7.41-7.49 (m, 2H), 7.7 (t, J=6.2 Hz, 1H).

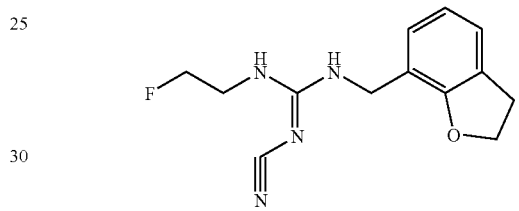

Synthesis of 1-(2,3-dihydro-benzofuran-7-ylmethyl)-3-(2-fluoro-ethyl)-cyanoguanidine The desired starting amine was obtained from the commercially available 2,3-dihydrobenzofuran according to the protocol described in the scheme below. The title compound was thus obtained from this amine according to general procedure A described above.

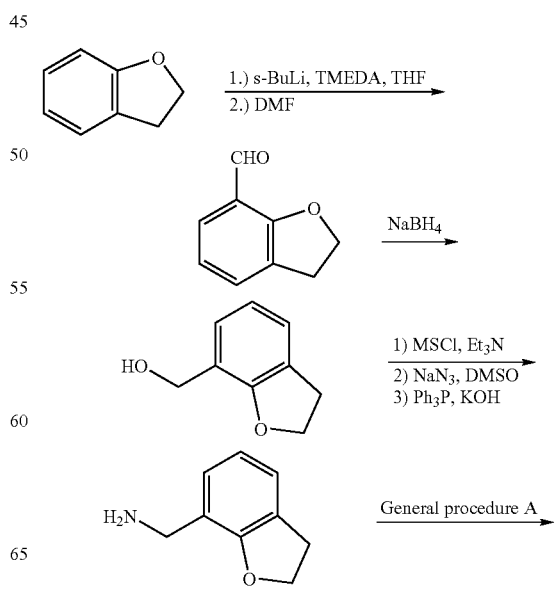

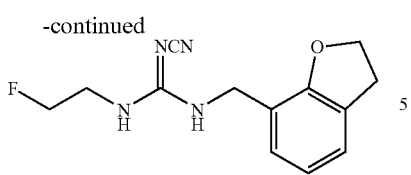

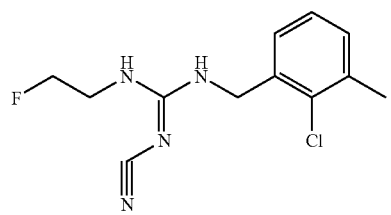

Synthesis of 1-(2-chloro-3-methyl-benzyl)-3-(2-fluoro-ethyl)-cyanoguanidine

The desired starting amine was prepared from 2-chloro-m-xylene according to the procedures shown in the scheme below. The title compound was thus obtained from this amine according to general procedure A described above.

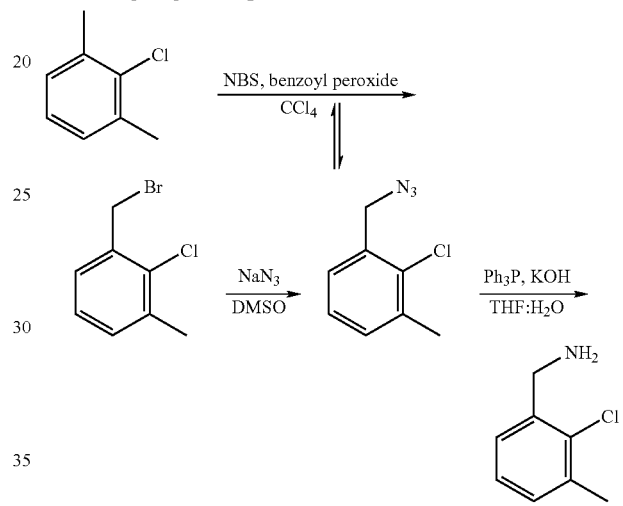

2,3-Dihydro-benzofuran-7-carbaldehyde: sec-BuLi (20.00 ml, 1.4 M in cyclohexane, 28.00 mmol) was added to a solution of 2,3-dihydro-benzofuran (2.40 mL, 21.30 mmol) and TMEDA (10.00 mL) in THF at −20° C. The resulting mixture was stirred for 1 hour, then DMF (3.00 mL, 38.75 mmol) was added and stirring was continued for another 30 minutes. The reaction mixture was quenched with water and diluted with ether. The resulting solution was washed with brine, dried over MgSO$_4$ and concentrated to afford the desired title aldehyde[i].

[i] Tasker, Andrew S.; Sorensen, Bryan K.; Jae, Hwan-Soo; Winn, Martin; Geldern, Thomas W. von; et al. *J. Med. Chem.* 1997, 40, 322-330.

(2,3-Dihydro-benzofuran-7-yl)-methanol: 2,3-Dihydro-benzofuran-7-carbaldehyde (1.50 g, 10.20 mmol) was dissolved in ether, then cooled to 0° C., NaBH$_4$ (400 mg, 10.57 mmol) in MeOH (5.00 mL) was added. The resulting reaction mixture was stirred for 30 min, then saturated ammonium chloride was added. The mixture was extracted with ether, and the combined organic phases were washed with brine, then dried over magnesium sulfate and concentrated to afford the desired alcohol.

C-(2,3-Dihydro-benzofuran-7-yl)-methylamine: (2,3-dihydro-benzofuran-7-yl)-methanol (1.50 g, 10.00 mmol) was dissolved in dichloromethane and cooled to −55° C., then MsCl (1.30 mL, 16.80 mmol) was added, followed by addition of Et$_3$N (3.0 mL, 21.52 mmol). The resulting reaction mixture was stirred at this temperature for 2 hours, then saturated aq ammonium chloride was added. The reaction mixture was extracted with ether. The combined organic phases were washed with brine, then dried over magnesium sulfate and concentrated to give the crude mesylate. The mesylate was then dissolved in DMSO, and treated with NaN$_3$ (1.30 g, 20.00 mmol) at room temperature for 14 hours. The reaction mixture was diluted with water, and extracted with ether. The combined organic phases were washed with water, brine, and then dried over magnesium sulfate and concentrated to afford the desired azide. This azido compound was then dissolved in THF:H$_2$O (3:1), Ph$_3$P (2.70 g, 10.29 mmol) was added, followed by KOH (600 mg, 10.69 mmol). The resulting mixture was stirred for 14 hours. The reaction mixture was then diluted with H$_2$O and slowly acidified with HCl and the aqueous layer was washed with Et$_2$O (3×50 mL). The aqueous layer was then basified with NaOH (pH 14) and extracted with Et$_2$O (3×50 mL). The combined organic extracts were washed with H$_2$O (1×25 mL), brine (1×25 mL), dried over K$_2$CO$_3$ and concentrated to give the desired title amine.

1-(2,3-Dihydro-benzofuran-7-ylmethyl)-3-(2-fluoro-ethyl)-cyanoguanidine: The title compound was obtained from (2,3-dihydro-benzofuran-7-yl)-methylamine (1.40 g, 9.40 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-d$_6$) □ 3.2 (t, J=8.8 Hz, 2H), 3.39-3.54 (m, 2H), 4.3 (d, J=6.7 Hz, 2H), 4.4 (t, J=5.0 Hz, 1H), 4.47-4.60 (m, 3H), 6.8 (t, J=7.6, 7.0 Hz, 1H), 7.0 (d, J=7.6 Hz, 1H), 7.10-7.22 (m, 2H), 7.4 (t, J=5.9, 5.3 Hz, 1H).

1-Bromomethyl-2-chloro-3-methyl-benzene[ii]: A solution of 2-chloro-m-xylene (5.00 g, 35.60 mmol), NBS (5.70 g, 32.03 mmol), and a catalytic amount of benzoyl peroxide (100 mg) in CCl$_4$ was refluxed for 1 hour. After cooling to room temperature the resulting mixture was filtered and the filtrate was distilled off. Purification by column chromatography using pentane as eluant followed by distillation afforded the title compound. Spectroscopic data: $^1$H NMR (300 MHz, CDCl$_3$) □ 2.39 (s, 3H), 4.61 (s, 2H), 7.08-7.23 (m, 2H), 7.25-7.30 (m, 1H).

[ii] Zhang, Jin-Tao; Dai, Wei; Harvey, Ronald G. *J. Org. Chem.* 1998, 63, 8125-8132.

1-Azidomethyl-2-chloro-3-methyl-benzene: A solution of 1-bromomethyl-2-chloro-3-methyl-benzene (3.68 g, 16.80 mmol) and NaN$_3$ (2.70 g, 41.53 mmol) in DMSO was stirred at 55° C. for 14 hours. The reaction mixture was then cooled to room temperature, water was added and the resulting mixture was extracted with Et$_2$O (3×100 mL). The combined organic phases were washed with H$_2$O (2×100 mL) and brine (1×100 mL), then dried over MgSO$_4$ and concentrated to afford the title azido compound. Spectroscopic data: $^1$H NMR (300 MHz, CDClCl$_3$) □2.37-2.45 (s, 3H), 4.49 (s, 2H), 7.15-7.27 (m, 3H).

2-Chloro-3-methyl-benzylamine: 1-Azidomethyl-2-chloro-3-methyl-benzene (2.99 g, 16.50 mmol) was dissolved in THF:H$_2$O (3:1), triphenyl phosphine (4.40 g, 16.78 mmol) was added, followed by KOH (923 mg, 16.45 mmol) and the resulting mixture was stirred for 14 hours. The reaction mixture was then diluted with H$_2$O, slowly acidified with HCl and the resulting aqueous layer was washed with Et$_2$O (3×50 mL). The aqueous layer was then basified with NaOH (pH 14), extracted with Et₂O (3×100 mL). The combined organic phases were washed with H₂O (1×50 mL) and brine (1×50 mL), then dried over K₂CO₃ and concentrated to give the title amine.

1-(2-Chloro-3-methyl-benzyl)-3-(2-fluoro-ethyl)-cyanoguanidine: The title compound was obtained from 2-chloro-3-methyl-benzylamine (2.80 g, 18.00 mmol) and 1-(2-fluoro-ethyl)-2-phenyl-3-cyanoisourea (2.00 g, 9.65 mmol) according to the protocols as outlined in general procedure A above. Spectroscopic data: $^1$H NMR (300 MHz, DMSO-dd₆) ☐ 2.4 (s, 3H), 3.38-3.48 (m, 1H), 3.48-3.59 (m, 1H), 4.35-4.47 (m, 3H), 4.6 (t, J=5.0 Hz, 1H), 7.03-7.13 (m, 1H), 7.21-7.35 (m, 3H), 7.6 (t, J=5.9, 5.3 Hz, 1H). $^{13}$C NMR (75 MHz, DMSO-d₆) ☐ 20.5, 42.3 (d, J=21.8 Hz), 43.5, 82.7 (d, J=166.4 Hz), 118.3, 125.8, 127.2 (2C), 130.3, 132.6, 136.6, 160.3.

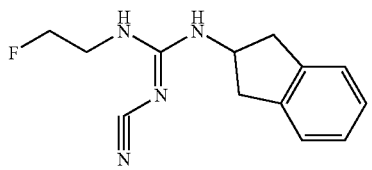

Synthesis of
1-(2-fluoro-ethyl)-3-indan-2-yl-cyanoguanidine

The title compound was generated from the commercially available indan-2-ylamine according to the general procedure A described above.

1-(2-Fluoro-ethyl)-3-indan-2-yl-cyanoguanidine: The title compound was obtained from indan-2-ylamine (1.20 g, 9.01 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd₆) ☐ 2.85-2.98 (m, 2H), 3.14-3.27 (m, 2H), 3.40-3.55 (m, 2H), 4.0 (q, J=7.0 Hz, 1H), 4.37-4.50 (m, 1H), 4.6 (t, J=5.0 Hz, 1H), 7.11-7.25 (m, 6H).

General Procedure B for the Synthesis of fluoroethyl Substituted Indan Cyanoguanidines

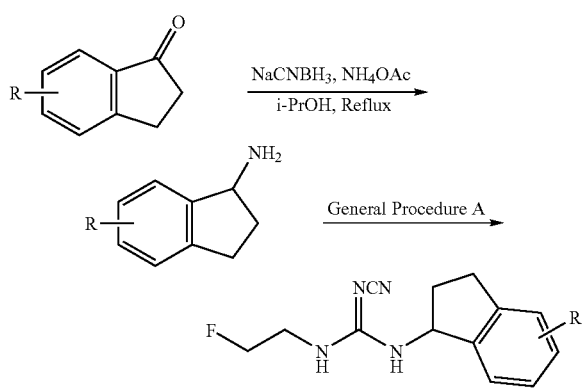

NaBH₃CN (7.0 eq) was added to a solution of an indanone in isopropanol. NH₄OAc (30 eq) was then added and the resulting mixture was stirred at room temperature for 4 hours, then refluxed for 22 hours. After cooling to room temperature, the reaction mixture was quenched with 200 mL of 2.5 N aq. NaOH. The layers were then separated and the aqueous layer was extracted with CH₂Cl₂. The combined organic extracts were washed with H₂O (75 mL), dried over K₂CO₃ and concentrated to give the desired indan amine. The final fluoroethyl cyanoguanidines were thus obtained according to the protocol described in General Procedure A.

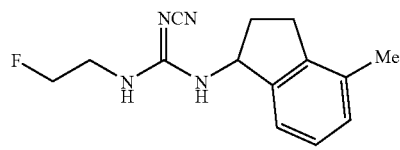

Synthesis of 1-(2-fluoro-ethyl)-3-(4-methyl-indan-1-yl)-cyanoguanidine

The title compound was generated from the commercially available 4-methylindanone according to general procedure B described above. The intermediate 4-methylindan-1-ylamine was isolated and characterized.

4-Methyl-indan-1-ylamine: The title amine was generated from 4-methyl-indan-1-one (5.00 g, 34.20 mmol), NaBH₃CN (15.00 g, 0.24 mol) and NH₄OAc (79.00 g, 1.02 mol) according to the protocols as outlined in general procedure B described above.

1-(2-Fluoro-ethyl)-3-(4-methyl-indan-1-yl)-cyanoguanidine: The title compound was obtained from 4-methyl-indan-1-ylamine (5.00 g, 33.96 mmol) and 1-(2-fluoro-ethyl)-2-phenyl-3-cyanoisourea (3.80 g, 18.34 mmol) according to the protocols as outlined in general procedure A above. Spectroscopic data: $^1$H NMR (300 MHz, DMSO-dd₆) ☐ 11.83-1.96 (m, 1H), 2.2 (s, 3H), 2.38-2.51 (m, 1H), 2.61-2.74 (m, 1H), 2.83-2.95 (m, 1H), 3.40-3.48 (m, 1H), 3.52-3.56 (m, 1H), 4.4 (t, J=5.0 Hz, 1H), 4.6 (t, J=5.0 Hz, 1H), 5.3 (q, J=7.9 Hz, 1H), 7.02-7.15 (m, 3H), 7.19-7.28 (m, 2H). $^{13}$C NMR (75 MHz, DMSO-dd₆) ☐ 19.1, 28.8, 33.0, 42.2 (d, J=21.8 Hz), 57.4, 82.8 (d, J=166.4 Hz), 118.4, 121.9, 127.3, 128.9, 134.2, 142.4, 143.5, 159.9.

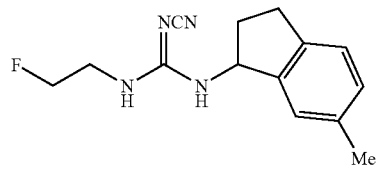

Synthesis of 1-(2-fluoro-ethyl)-3-(6-methyl-indan-1-yl)-cyanoguanidine

The title compound was generated from the commercially available 6-methylindanone according to general procedure B described above. The intermediate 6-methylindan-1-ylamine was isolated and characterized.

6-Methyl-indan-1-ylamine: The title amine was obtained from 6-methyl-indan-1-one (5.00 g, 34.20 mmol), NaBH₃CN (15.00 g, 0.24 mol) and NH₄OAc (79.00 g, 1.02 mol) according to the protocols as outlined in general procedure B described above.

1-(2-Fluoro-ethyl)-3-(6-methyl-indan-1-yl)-cyanoguanidine: The title compound was obtained 6-methyl-indan-1- ylamine (1.30 g, 8.80 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd$_6$) ☐ 1.82-1.95 (m, 1H), 2.3 (s, 3H), 2.34-2.48 (m, 1H), 2.65-2.78 (m, 1H), 2.81-2.93 (m, 1H), 3.43-3.58 (m, 2H), 4.4 (t, J=5.0 Hz, 1H), 4.6 (t, J=5.0 Hz, 1H), 5.2 (q, J=7.9 Hz, 1H), 6.99-7.07 (m, 2H), 7.09-7.16 (m, 1H), 7.21-7.30 (m, 2H).

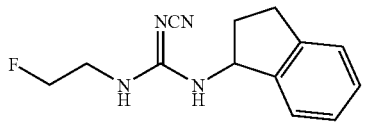

Synthesis of 1-(2-fluoro-ethyl)-3-(indan-1-yl)-cyanoguanidine

The title compound was generated from the commercially available indan-1-ylamine according to general procedure A described above.

1-(2-Fluoro-ethyl)-3-indan-1-yl-cyanoguanidine: The title compound was obtained from indan-1-ylamine (1.20 g, 9.01 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd$_6$) ☐ 1.84-1.99 (m, 1H), 2.37-2.51 (m, 1H), 2.71-2.84 (m, 1H), 2.88-2.99 (m, 1H), 3.43-3.59 (m, 2H), 4.4 (t, J=5.0 Hz, 1H), 4.6 (t, J=5.0 Hz, 1H), 5.3 (q, J=8.2, 7.6 Hz, 1H), 7.19-7.32 (m, 6H). $^{13}$C NMR (75 MHz, DMSO-dd$_6$) ☐ 30.3, 33.6, 42.3 (d, J=20.7 Hz), 57.1, 82.8 (d, J=165.2 Hz), 118.4, 124.5, 125.2, 127.1, 128.3, 143.5, 143.9, 160.0.

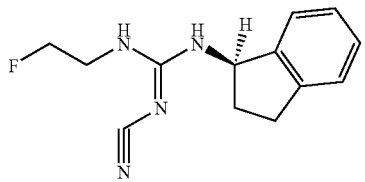

Synthesis of (S)-(+)-1-(2-fluoro-ethyl)-3-(indan-1-yl)-cyanoguanidine

The title compound was generated from the commercially available (S)-(+)-indan-1-ylamine according to general procedure A described above.

(S)-(+)-1-(2-Fluoro-ethyl)-3-(indan-1-yl)-cyanoguanidine: The title compound was obtained from (S)-(+)-indan-1-ylamine (1.20 g, 9.01 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd$_6$) ☐ 1.84-1.99 (m, 1H), 2.37-2.52 (m, 1H), 2.71-2.84 (m, 1H), 2.88-2.99 (m, 1H), 3.42-3.58 (m, 2H), 4.4 (t, J=5.3, 4.7 Hz, 1H), 4.6 (t, J=5.0 Hz, 1H), 5.3 (q, J=8.2, 7.6 Hz, 1H), 7.18-7.32 (m, 6H). $^{13}$C NMR (75 MHz, DMSO-d$_6$) ☐ 30.3, 33.6, 42.3 (d, J=20.7 Hz), 57.2, 82.8 (d, J=166.4 Hz), 118.5, 124.5, 125.2, 127.1, 128.3, 143.5, 143.9, 160.0.

General Procedure C for the Synthesis of Fluoroethyl Substituted Indan Cyanoguanidines

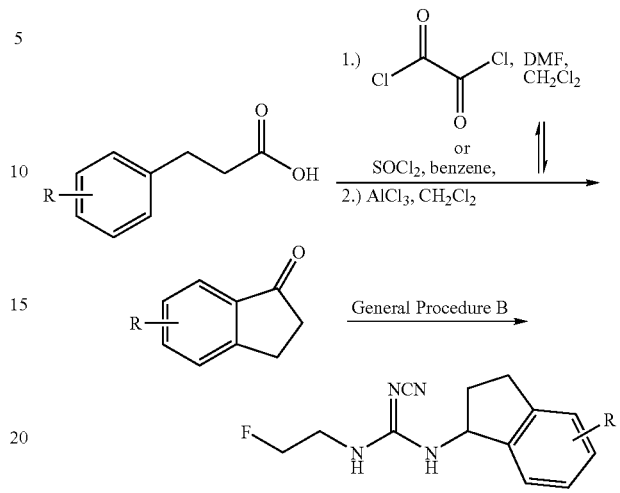

To a solution of 3-(substituted-phenyl)-propionic acid in CH$_2$Cl$_2$ at 0° C. was added oxalyl chloride (1.5 eq) followed by 2-3 drops of DMF (in case of SOCl$_2$, benzene would be used as solvent, and the reaction mixture would be refluxed for 3 hours). The resulting mixture was stirred until no more gas evolution was observed. After concentration of the reaction mixture, the residue was dissolved in CH$_2$Cl$_2$, cooled to 0° C., and AlCl$_3$ (1.0 eq) was added in 3 batches at 3-minute interval. After stirring for 1 hour, the reaction mixture was quenched in ice-water and the layers were separated. The aqueous layer was extracted with Et$_2$O (3×150 mL) and the combined organic extracts were washed with H$_2$O (3×100 mL), saturated NaHCO$_3$ (3×100 mL), brine (1×100 mL), dried over MgSO$_4$ and concentrated. Purification by column chromatography using hexane:EtOAc (4.5:0.5) as eluant gave the desired substituted indanone. The indanone was thus converted to the desired fluoroethyl cyanoguanidines via the protocols described in general procedure B.

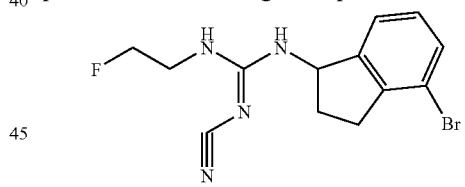

Synthesis of 1-(4-bromo-indan-1-yl)-3-(2-fluoro-ethyl)-cyanoguanidine

The title compound was generated from the commercially available 3-(2-bromophenyl)propionic acid according to general procedure C described above. The intermediates 4-bromoindan-1-one and 4-bromoindan-1-ylamine were separated and characterized.

4-Bromo-indan-1-one[iii]: The title compound was obtained from 3-(2-bromo-phenyl)-propionic acid (10.00 g, 43.70 mmol), SOCl$_2$ (5.00 mL, 68.55 mmol) and AlCl$_3$ (6.40 g, 48.00 mmol) according to the protocols as outlined in general procedure C.

[iii] Faller, P. Bull. Soc. Chim. Fr. 1966, 3618-3625.

4-Bromo-indan-1-ylamine: The title amine was generated from 4-bromo-indan-1-one (5.00 g, 23.70 mmol), NaBH$_3$CN (10.40 g, 165.50 mmol) and NH$_4$OAc (54.80 g, 710.95 mmol) according to the protocols as outlined in general procedure B described above.

1-(4-Bromo-indan-1-yl)-3-(2-fluoro-ethyl)-cyanoguanidine: The title compound was obtained from 4-bromo-indan-1-ylamine (1.90 g, 8.96 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd$_6$) ☐ 1.88-2.01 (m, 1H), 2.40-2.53 (m, 1H), 2.70-2.84 (m, 1H), 2.89-2.99 (m, 1H), 3.41-3.57 (m, 2H), 4.4 (t, J=5.3 Hz, 1H), 4.6 (t, J=5.0 Hz, 1H), 5.4 (q, J=7.6 Hz, 1H), 7.16-7.26 (m, 2H), 7.3 (t, J=5.9, 5.3 Hz, 1H), 7.4 (d, J=8.5 Hz, 1H), 7.5 (d, J=7.6 Hz, 1H). $^{13}$C NMR (75 MHz, DMSO-d$_6$) ☐ 31.8, 32.4, 42.3 (d, J=20.7 Hz), 57.9, 82.7 (d, J=166.4 Hz), 118.3, 120.0, 124.0, 129.5, 131.1, 143.7, 146.3, 159.8.

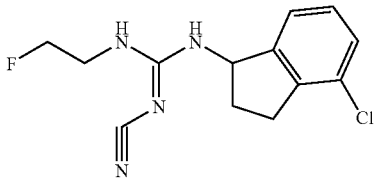

Synthesis of 1-(4-chloro-indan-1-yl)-3-(2-fluoro-ethyl)-cyanoguanidine

The desired 3-(2-chlorophenyl)propionic acid was obtained from hydrogenation of the commercially available 3-(2-chlorophenyl)acrylic acid. The title compound was thus generated from the 3-(2-chlorophenyl)propionic acid according to general procedure C described above. The intermediates 4-chloroindan-1-one and 4-chloroindan-1-ylamine were separated and characterized.

4-Chloro-indan-1-one[iv]: 3-(2-chloro-phenyl)-acrylic acid (10.00 g, 55.00 mmol) in THF was mixed with Rh/Al$_2$O$_3$ (500 mg) and hydrogenated for 14 hours. The reaction mixture was filtered through celite and the filtrate was concentrated to give 3-(2-chloro-phenyl)-propionic acid. 3-(2-chloro-phenyl)-propionic acid (10.0 g, 43.70 mmol) was then reacted with SOCl$_2$ (6.00 mL, 82.26 mmol) and AlCl$_3$ (8.00 g, 60.00 mmol) according to the protocols as outlined in general procedure C to afford the title chloroindanone.

[iv] Berrier, C.; Gesson, J. P.; Jacquesy, J. C.; Renoux, A. *Tetrahedron* 1984, 40, 4973-4980.

4-Chloro-indan-1-ylamine[v]: 4-Chloro-indan-1-one (5.00 g, 30.10 mmole), NaBH$_3$CN (13.20 g, 0.21 mol) and NH$_4$OAc (70.00 g, 0.91 mol) in isopropanol were reacted according to the protocols as outlined in general procedure B to give the desired title amine.

[v] Eli Lilly and Co. Indianapolis, Ind. (V.St.A), DE 2812578, 1978, Chem. Abstr. 90, 54730.

1-(4-Chloro-indan-1-yl)-3-(2-fluoro-ethyl)-cyanoguanidine: The title compound was obtained from 4-chloro-indan-1-ylamine (1.50 g, 9.00 mmol) and 1-(2-fluoro-ethyl)-2-phenyl-3-cyanoisourea (1.00 g, 4.83 mmol) outlined in general procedure A above. Spectroscopic data: $^1$H NMR (300 MHz, DMSO-dd$_6$) ☐ 1.88-2.02 (m, 1H), 2.40-2.53 (m, 1H), 2.73-2.86 (m, 1H), 2.90-3.04 (m, 1H), 3.41-3.57 (m, 2H), 4.4 (t, J=5.0 Hz, 1H), 4.6 (t, J=5.3 Hz, 1H), 5.4 (q, J=8.2, 7.6 Hz, 1H), 7.2 (t, J=8.2, 7.0 Hz, 1H), 7.25-7.35 (m, 3H), 7.4 (d, J=8.5 Hz, 1H). $^{13}$C NMR (75 MHz, DMSO-d$_6$) ☐ 29.6, 32.6, 42.3 (d, J=20.7 Hz), 57.6, 82.7 (d, J=166.4 Hz), 118.3, 123.4, 128.1, 129.3, 130.4, 141.6, 146.5, 159.8.

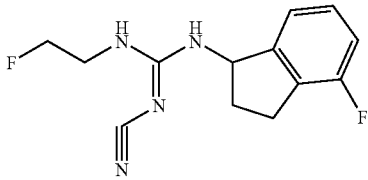

Synthesis of 1-(2-fluoro-ethyl)-3-(4-fluoro-indan-1-yl)-cyanoguanidine

The desired 3-(2-fluorophenyl)propionic acid was obtained from hydrogenation of the commercially available 3-(2-fluorophenyl)acrylic acid. The title compound was thus generated from this acid according to general procedure C described above. The intermediates 4-fluoroindan-1-one and 4-fluoroindan-1-ylamine were separated and characterized.

4-Fluoro-indan-1-one[vi]: 3-(2-fluoro-phenyl)-acrylic acid (10.00 g, 60.30 mmol) in THF was mixed with Rh/Al$_2$O$_3$ (500 mg) and hydrogenated for 14 hours. The reaction mixture was filtered through celite and the filtrate was concentrated to give 3-(2-fluoro-phenyl)-propionic acid. 3-(2-chloro-phenyl)-propionic acid (10.0 g, 43.70 mmol) was then reacted with SOCl$_2$ (6.60 mL, 90.48 mmol) and AlCl$_3$ (9.00 g, 67.50 mmol) according to the protocols as outlined in general procedure C to afford the title compound.

[vi] Musso, David L.; Cochran, Felicia R.; Kelley, James L.; McLean, Ed W.; Selph, Jeffrey L.; Rigdon, Greg C.; Orr, G. Faye; Davis, Ronda G.; Cooper, Barrett R.; Styles, Virgil L.; Thompson, James B.; Hall, William R. *J. Med. Chem.* 2003, 46, 399-408.

4-Fluoro-indan-1-ylamine: The title compound was obtained from 4-fluoro-indan-1-one (5.00 g, 33.30 mmol), NaBH$_3$CN (14.70 g, 0.23 mol) and NH$_4$OAc (77.00 g, 1.00 mol) according to the protocols as outlined in general procedure B described above.

1-(2-Fluoro-ethyl)-3-(4-fluoro-indan-1-yl)-cyanoguanidine: The title compound was obtained from 4-fluoro-indan-1-ylamine (1.40 g, 9.30 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd$_6$) ☐ 1.90-2.04 (m, 1H), 2.42-2.55 (m, 1H), 2.71-2.85 (m, 1H), 2.93-3.06 (m, 1H), 3.44-3.59 (m, 2H), 4.4 (t, J=5.0 Hz, 1H), 4.6 (t, J=4.7 Hz, 1H), 5.4 (q, J=8.2 Hz, 1H), 7.03-7.13 (m, 2H), 7.19-7.48 (m, 3H). $^{13}$C NMR (75 MHz, DMSO-d$_6$) ☐ 26.1, 33.3, 42.3 (d, J=20.7 Hz), 57.2 (d, J=2.3 Hz), 82.7 (d, J=166.4 Hz), 114.7 (d, J=20.7 Hz), 118.3, 120.7 (d, J=2.3 Hz), 129.3 (d, J=6.9 Hz), 129.5 (d, J=5.7 Hz), 147.9 (d, J=5.7 Hz), 159.3 (d, J=244.4 Hz), 159.9.

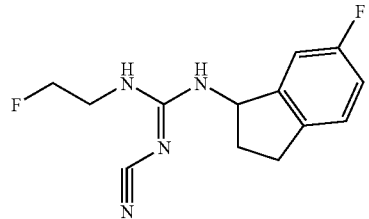

Synthesis of 1-(2-fluoro-ethyl)-3-(6-fluoro-indan-1-yl)-cyanoguanidine

The desired 3-(4-fluorophenyl)propionic acid was obtained from hydrogenation of the commercially available 3-(4-fluorophenyl)acrylic acid. The title compound was thus generated from this acid according to general procedure C described above. The intermediates 6-fluoroindan-1-one and 6-fluoroindan-1-ylamine were separated and characterized.

6-Fluoro-indan-1-one[6]: 3-(4-Fluoro-phenyl)-acrylic acid (25.00 g, 151.00 mmol) in THF was mixed with Rh/Al$_2$O$_3$ (1.00 g) and hydrogenated for 14 hours. The reaction mixture was filtered through celite and the filtrate was concentrated to give 3-(4-fluoro-phenyl)-propionic acid. 3-(4-fluoro-phenyl)-propionic acid was then reacted with SOCl$_2$ (16.50 mL, 0.23 mol) and AlCl₃ (22.00 g, 0.16 mol) according to the protocols as outlined in general procedure C to afford the title compound.

6-Fluoro-indan-1-ylamine: The title amine was obtained from 6-fluoro-indan-1-one (5.00 g, 33.30 mmol), NaBH₃CN (14.70 g, 0.23 mol) and NH₄OAc (77.00 g, 1.00 mol) according to the protocols as outlined in general procedure B described above.

1-(2-Fluoro-ethyl)-3-(6-fluoro-indan-1-yl)-cyanoguanidine: The title compound was obtained from 6-fluoro-indan-1-ylamine (1.40 g, 9.30 mmol) and 1-(2-fluoro-ethyl)-2-phenyl-3-cyanoisourea (1.00 g, 4.83 mmol) according to the protocols as outlined in general procedure A above. Spectroscopic data: ¹H NMR (300 MHz, DMSO-dd₆) □ 1.87-2.02 (m, 1H), 2.39-2.54 (m, 1H), 2.68-2.81 (m, 1H), 2.85-2.96 (m, 1H), 3.43-3.58 (m, 2H), 4.4 (t, J=5.3, 4.7 Hz, 1H), 4.6 (t, J=5.0 Hz, 1H), 5.3 (q, J=8.2, 7.3 Hz, 1H), 6.96-7.10 (m, 2H), 7.24-7.39 (m, 3H). ¹³C NMR (75 MHz, DMSO-d₆) □ 29.5, 34.1, 42.3 (d, J=20.7 Hz), 57.1, 82.8 (d, J=166.4 Hz), 111.3 (d, J=21.8 Hz), 115.1 (d, J=21.8 Hz), 118.4, 126.5 (d, J=8.0 Hz), 139.3 (d, J=2.3 Hz), 146.3 (d, J=6.9 Hz), 160.0, 162.1 (d, J=242.1 Hz).

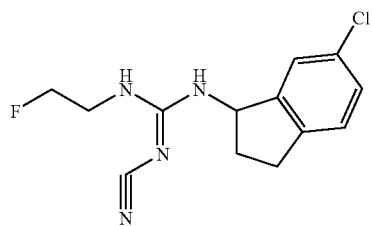

Synthesis of 1-(6-chloro-indan-1-yl)-3-(2-fluoro-ethyl)-cyanoguanidine

The desired 3-(4-chlorophenyl)propionic acid was obtained from hydrogenation of the commercially available 3-(4-chlorophenyl)acrylic acid. The title compound was thus generated from this acid according to general procedure C described above. The intermediates 6-chloroindan-1-one and 6-chloroindan-1-ylamine were separated and characterized.

6-Chloro-indan-1-one⁶: 3-(4-Chloro-phenyl)-acrylic acid (25.00 g, 0.14 mol) in THF was mixed with Rh/Al₂O₃ (1.00 g) and hydrogenated for 14 hours. The reaction mixture was filtered through celite and the filtrate was concentrated to give 3-(4-chloro-phenyl)-propionic acid. 3-(4-chloro-phenyl)-propionic acid was then reacted with SOCl₂ (15.00 mL, 0.21 mol) and AlCl₃ (20.20 g, 0.15 mol) according to the protocols as outlined in general procedure C to afford the title compound.

6-Chloro-indan-1-ylamine: The title compound was obtained from 6-Chloro-indan-1-one (5.00 g, 30.00 mmol), NaBH₃CN (13.30 g, 0.21 mol) and NH₄OAc (70.00 g, 0.91 mol) according to the protocols as outlined in general procedure B.

1-(6-Chloro-indan-1-yl)-3-(2-fluoro-ethyl)-cyanoguanidine: The title compound was obtained from 6-chloro-indan-1-ylamine (1.50 g, 9.01 mmol) and 1-(2-fluoro-ethyl)-2-phenyl-3-cyanoisourea (1.00 g, 4.83 mmol) according to the protocols as outlined in general procedure A above. Spectroscopic data: ¹H NMR (300 MHz, DMSO-dd₆) □ 1.87-2.00 (m, 1H), 2.39-2.52 (m, 1H), 2.69-2.82 (m, 1H), 2.85-2.97 (m, 1H), 3.43-3.59 (m, 2H), 4.4 (t, J=5.0 Hz, 1H), 4.6 (t, J=5.3, 4.7 Hz, 1H), 5.3 (q, J=8.2 Hz, 1H), 7.2 (br s, 1H), 7.25-7.33 (m, 3H), 7.4 (d, J=8.2 Hz, 1H). ¹³C NMR (75 MHz, DMSO-d₆) □ 29.8, 33.8, 42.3 (d, J=20.7 Hz), 57.0, 82.8 (d, J=166.4 Hz), 118.3, 124.5, 126.9, 128.1, 131.6, 142.5, 146.4, 160.0.

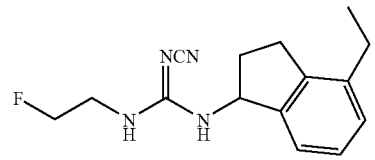

Synthesis of 1-(4-ethyl-indan-1-yl)-3-(2-fluoro-ethyl)-cyanoguanidine

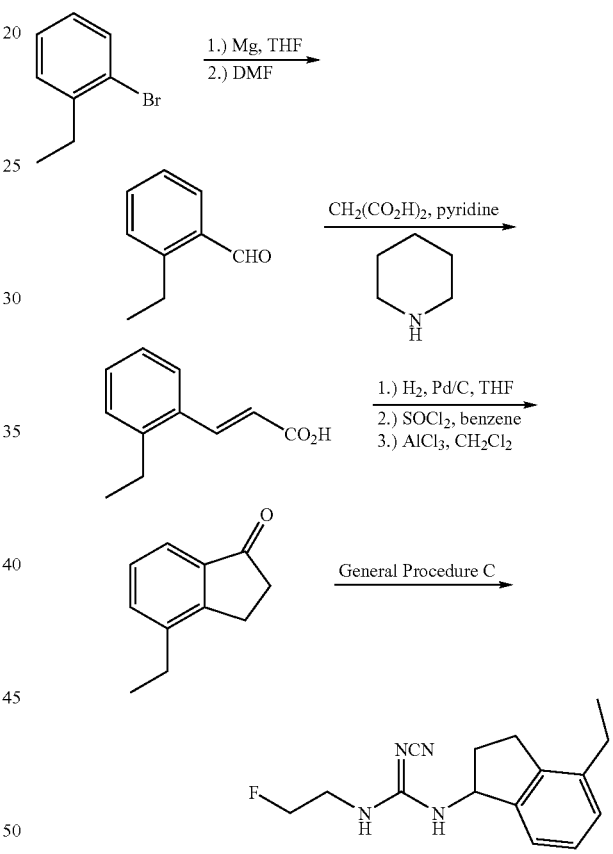

The title compound was generated from commercially available 1-bromo2-ethylbenzene according to the scheme above. The intermediates 2-ethylbenzaldehyde, 3-(2-ethylphenyl)-acrylic acid, 4-ethyl-1-indanone and 4-ethylindan-1-ylamine were isolated and characterized.

2-Ethyl-benzaldehyde^vii: A solution of 1-bromo-2-ethylbenzene (5.00 g, 27.02 mmol), Mg (4.00 g, 0.16 mol) and a catalytic amount of I2 in THF was refluxed for 2 hours. After cooling the reaction mixture to 0° C., DMF (10.00 mL) was added and the mixture was stirred for 30 minutes. It was then quenched with 10% HCl and the resulting solution was extracted with Et₂O (3×200 mL). The combined organic extracts were washed with H₂O (2×200 mL), brine (1×200 mL), dried over MgSO₄ and concentrated to give the title compound.

[vii] Nakamura, Y.; O-kawa, K.; Minami, S.; Ogawa, T.; Tobita, S.; Nishimura, J. J. Org. Chem. 2002, 67, 1247-1252.

3-(2-Ethyl-phenyl)-acrylic acid[viii]: To a solution of 2-ethyl-benzaldehyde (18.40 g, 0.14 mol) and malonic acid (28.00 g, 0.27 mol) in pyridine was added 10.00 mL of piperidine and the resulting mixture was slowly refluxed for 3 hours. After cooling to room temperature, the reaction mixture was diluted with ice water, acidified to pH<1. The resulting solid was filtered, washed with water and dried under vacuum to give the title compound.

[viii] Cope, A. C.; Liss, T. A.; Smith, D. S. J. Am. Chem. Soc. 1957, 79, 240-243.

4-Ethyl-indan-1-one: 3-(2-Ethyl-phenyl)-acrylic acid (17.00 g, 96.48 mmol) in THF was mixed with Pd/C (1.50 g) and hydrogenated at 50 psi for 6 hours. The resulting mixture was filtered through a pad of celite and the filtrate was concentrated to give 3-(2-ethyl-phenyl)-propionic acid. The acid was reacted with $SOCl_2$ (5.00 mL, 68.55 mmol) and $AlCl_3$ (6.70 g, 50.25 mmol) according to the protocols as outlined in general procedure C to give the title compound.

4-Ethyl-indan-1-ylamine: 4-Ethyl-indan-1-one (5.00 g, 31.21 mmol), $NaBH_3CN$ (13.70 g, 0.22 mol) and $NH_4OAc$ (72.00 g, 0.93 mol) in isopropanol were reacted according to the protocols as outlined in general procedure B to give the desired amine.

1-(4-Ethyl-indan-1-yl)-3-(2-fluoro-ethyl)-cyanoguanidine: The title compound was obtained from 4-ethyl-indan-1-ylamine (1.50 g, 9.30 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd$_6$) □ 1.1 (t, J=7.6 Hz, 3H), 1.82-1.97 (m, 1H), 2.41-2.46 (m, 1H), 2.6 (q, J=7.6 Hz, 2H), 2.65-2.77 (m, 1H), 2.88-2.99 (m, 1H), 3.41-3.57 (m, 2H), 4.4 (t, J=5.0 Hz, 1H), 4.6 (t, J=5.0 Hz, 1H), 5.3 (q, J=8.5, 7.9 Hz, 1H), 7.1 (t, J=7.3 Hz, 2H), 7.2 (t, J=7.6 Hz, 1H), 7.24-7.33 (m, 2H). $^{13}$C NMR (75 MHz, DMSO-d$_6$) □ 15.1, 26.2, 28.4, 33.1, 42.2 (d, J=20.7 Hz), 57.3, 82.8 (d, J=166.4 Hz), 118.5, 122.0, 127.3, 127.5, 140.3, 141.6, 143.7, 159.9.

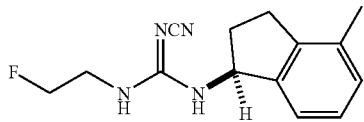

Synthesis of (S)-(+)-1-(2-fluoro-ethyl)-3-(4-methyl-indan-1-yl)-cyanoguanidine

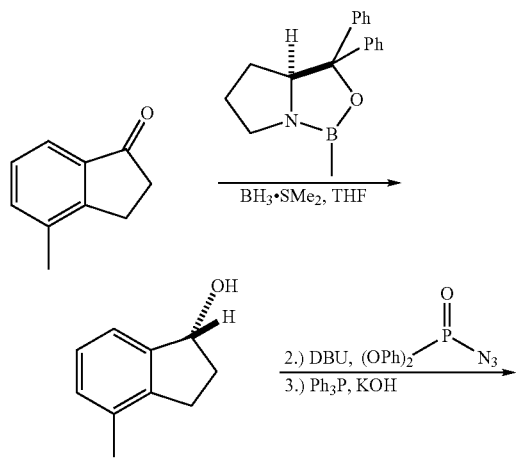

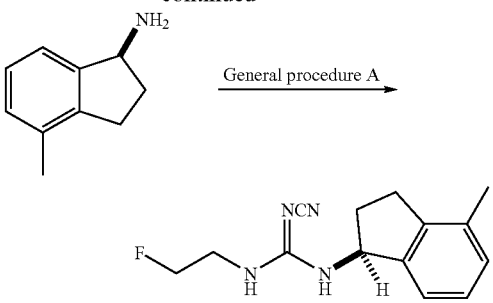

The desired chiral starting amine was generated from the commercially available 4-methylindan-1-one according to the chemistry described in the scheme above. The title compound was thus obtained from this amine according to general procedure A. The intermediates (R)-4-methyl-indan-1-ol and (S)-4-methyl-indan-1-ylamine were separated and characterized.

(R)-4-Methyl-indan-1-ol: To a solution of 4-methyl-indan-1-one (5.00 g, 34.20 mmole) and (S)-2-methyl-CBS-oxazaborolidine (5.00 mL, 1.0 M in THF, 5.00 mmol) in THF at -20° C. was added borane-methylsulfide (12.00 mL, 1.0 M in THF, 12.00 mmol) over 20 minutes. The resulting mixture was then stirred for 50 minutes and cooled to -30° C. Methanol (40.00 mL) was added and the resulting mixture was gradually warmed to room temperature and concentrated to give the crude alcohol.

(S)-4-Methyl-indan-1-ylamine: (R)-4-Methyl-indan-1-ol (34.20 mmol, crude taken from the previous step) was dissolved in toluene and cooled to 0° C., diphenylphosphoryl azide (8.80 mL, 40.83 mmol) was added. The resulting mixture was stirred for a few minutes and DBU (5.20 mL, 34.77 mmol) was added slowly. After stirring for 14 hours, the reaction mixture was diluted with toluene and washed with $H_2O$ (3×50 mL), brine (1×50 mL), dried over $MgSO_4$ and concentrated. Purification by column chromatography using hexane:EtOAc (4:1) as eluant gave the desired azido compound. This azido compound was then dissolved in THF:$H_2O$ (3:1), Ph$_3$P (7.80 g, 29.74 mmol) was added, followed by KOH (2.00 g, 35.64 mmol). The resulting mixture was stirred for 14 hours. The reaction mixture was then diluted with $H_2O$ and slowly acidified with HCl and the aqueous layer was washed with Et$_2$O (3×50 mL). The aqueous layer was then basified with NaOH (pH 14) and extracted with Et$_2$O (3×50 mL). The combined organic extracts were washed with $H_2O$ (1×25 mL), brine (1×25 mL), dried over $K_2CO_3$ and concentrated to give the desired indan amine.

(S)-(+)-1-(2-Fluoro-ethyl)-3-(4-methyl-indan-1-yl)-cyanoguanidine: The title compound was obtained from (S)-4-methyl-indan-1-ylamine (3.00 g, 20.38 mmol) and 1-(2-fluoro-ethyl)-2-phenyl-3-cyanoisourea (2.00 g, 9.66 mmol) according to the protocols as outlined in general procedure A above. Spectroscopic data: $^1$H NMR (300 MHz, DMSO-dd$_6$) □ 1.83-1.96 (m, 1H), 2.2 (s, 3H), 2.34-2.49 (m, 1H), 2.61-2.74 (m, 1H), 2.83-2.95 (m, 1H), 3.42-3.58 (m, 2H), 4.4 (t, J=5.3 Hz, 1H), 4.6 (t, J=5.0 Hz, 1H), 5.3 (q, J=7.9 Hz, 1H), 7.01-7.09 (m, 2H), 7.1 (t, J=7.3 Hz, 1H), 7.19-7.28 (m, 2H). $^{13}$C NMR (75 MHz, DMSO-d$_6$) □ 19.1, 28.8, 33.0, 42.2 (d, J=20.7 Hz), 57.4, 82.8 (d, J=166.4 Hz), 118.4, 121.9, 127.3, 128.9, 134.2, 142.4, 143.5, 159.9.

General Procedure D for the Synthesis of Fluoroethyl Substituted (1,2,3,4-Tetrahydronaphthalen-1-yl)cyanoguanidines

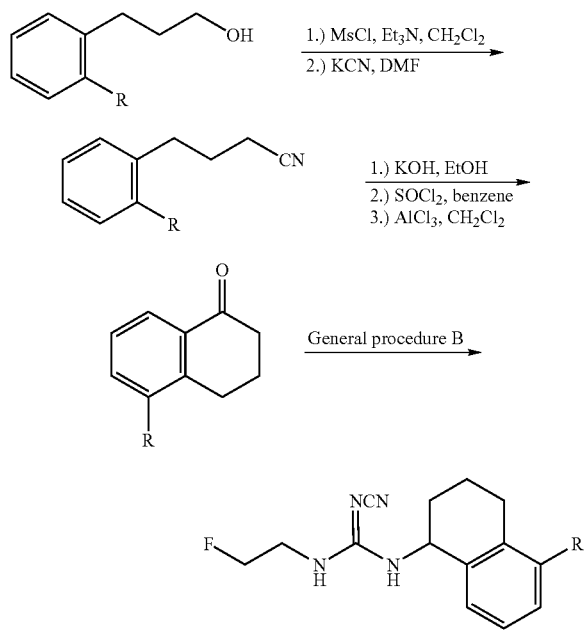

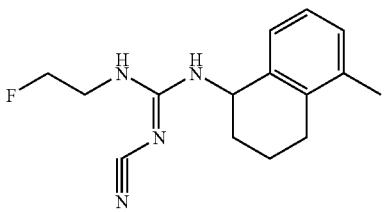

Synthesis of 1-(2-fluoro-ethyl)-3-(5-methyl-1,2,3,4-tetrahydro-naphthalen-1-yl)-cyanoguanidine

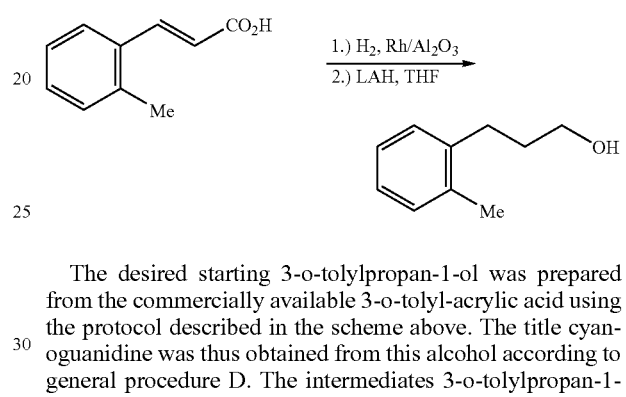

To a solution of 3-(2-substituted-phenyl)-propan-1-ol in CH$_2$Cl$_2$ at 0° C. was added Et$_3$N (2.0 eq) and MsCl (1.5 eq). The resulting mixture was stirred for 1 hour, then washed with H$_2$O (3×100 mL), brine (1×150 mL), dried over MgSO$_4$ and concentrated. The residue was dissolved in DMF and KCN (2.0 eq) was added and the resulting mixture was stirred at 75° C. for 14 hours. After cooling to room temperature, the reaction mixture was quenched into water and extracted with Et$_2$O (3×300 mL). The combined organic extracts were washed with H$_2$O (2×200 mL), brine (1×200 mL), dried over MgSO$_4$ and concentrated to give 4-(2-substituted-phenyl)-butyronitrile. This crude butyronitrile was taken up in ethanol and KOH (2 eq) was added. The resulting mixture was refluxed for 14 hours. The reaction mixture was cooled to room temperature, diluted with water and washed with Et$_2$O (2×150 mL). The aqueous layer was acidified with concentrated HCl and the resulting solution was extracted with Et$_2$O (3×300 mL). The combined organic extracts were washed with H$_2$O (2×200 mL), brine (1×200 mL), dried over MgSO$_4$ and concentrated to give 4-(2-substituted-phenyl)-butyric acid. The crude acid was then dissolved in benzene and SOCl$_2$ (1.5 eq) was added and the reaction mixture was refluxed for 4 hours. After cooling to room temperature, the reaction mixture was concentrated and the residue was taken up in CH$_2$Cl$_2$ and cooled to 0° C. AlCl$_3$ (1.1 eq) was added and the resulting mixture was stirred for 14 hours. The reaction mixture was quenched with HCl, washed with H$_2$O (2×200 mL), brine (1×200 mL), dried over MgSO$_4$ and concentrated to give 5-substituted-3,4-dihydro-2H-naphthalen-1-one. This ketone was thus converted into the desired fluoroethyl cyanoguanidine according to general procedure B.

The desired starting 3-o-tolylpropan-1-ol was prepared from the commercially available 3-o-tolyl-acrylic acid using the protocol described in the scheme above. The title cyanoguanidine was thus obtained from this alcohol according to general procedure D. The intermediates 3-o-tolylpropan-1-ol, 4-o-tolyl-butyronitrile, 5-methyl-3,4-dihydro-2H-naphthalen-1-one and 5-methyl-1,2,3,4-tetrahydro-naphthalen-1-ylamine were separated and characterized.

3-o-Tolyl-propan-1-ol[ix]: 3-o-Tolyl-acrylic acid (10.00 g, 62.00 mmol) in THF was mixed with Rh/Al$_2$O$_3$ (800 mg) and hydrogenated at 50 psi for 6 hours. The resulting mixture was filtered through a pad of celite and the filtrate was concentrated. The residue was dissolved in THF and cooled to 0° C. LAH (62.00 mL, 1.0 M in THF, 62.00 mmol) was added and the reaction mixture was stirred for 14 hours. The resulting mixture was quenched with NaOH and extracted with Et$_2$O (3×250 mL). The combined organic extracts were washed with H$_2$O (3×150 mL), brine (1×150 mL), dried over MgSO$_4$ and concentrated to give the title alcohol.

[ix] Stipanovic, B.; Pines, H. *J. Org. Chem.* 1969, 34, 2106-2113.

4-o-Tolyl-butyronitrile[x]: The title compound was obtained from 3-o-tolyl-propan-1-ol (taken from the previous step), Et$_3$N (17.20 mL, 0.12 mol), MsCl (7.60 mL, 98.19 mmol) and KCN (8.00 g, 0.12 mol) according to the protocols as outlined in general procedure D.

[x] Staab, Heinz A.; Nikolic, Susanne; Krieger, Claus *Eur. J. Org. Chem.* 1999, 6, 1459-1470.

5-Methyl-3,4-dihydro-2H-naphthalen-1-one[xi]: The title compound was obtained from 4-o-tolyl-butyronitrile (taken from the previous step), KOH (7.00 g, 124.75 mmol), SOCl$_2$ (7.00 mL, 95.96 mmol) and AlCl$_3$ (9.00 g, 67.50 mmol) according to the protocols as outlined in general procedure D.

[xi] Zhang, Xiaoyan; Angeles, Joseph E. De Los; He, Mei-Ying; Dalton, James T.; Shams, Gamal; et al. *J. Med. Chem.* 1997, 40, 3014-3024.

5-Methyl-1,2,3,4-tetrahydro-naphthalen-1-ylamine: The title amine was obtained from 5-methyl-3,4-dihydro-2H-naphthalen-1-one (7.00 g, 43.80 mmol), NaBH$_3$CN (19.30 g, 0.31 mol) and NH$_4$OAc (101.20 g, 1.31 mol) according to the protocols as outlined in general procedure B.

1-(2-Fluoro-ethyl)-3-(5-methyl-1,2,3,4-tetrahydro-naphthalen-1-yl)-cyanoguanidine: The title compound was obtained from 5-methyl-1,2,3,4-tetrahydro-naphthalen-1-ylamine (1.50 g, 9.30 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd$_6$) □ 1.61-2.01 (m, 4H), 2.1 (s, 3H), 2.48-2.62 (m, 2H), 3.41-3.57 (m, 2H), 4.4 (t, J=5.0 Hz, 1H), 4.5 (t, J=5.0 Hz, 1H), 4.90-5.03 (m, 1H), 7.00-7.11 (m, 3H), 7.14-7.23 (m, 2H). $^{13}$C NMR (75 MHz, DMSO-d$_6$) □ 19.9, 20.4, 26.7, 29.9, 42.2 (d, J=20.7 Hz), 50.6, 82.8 (d, J=166.4 Hz), 118.5, 126.1, 126.3, 128.9, 136.4, 136.6, 137.4, 159.6.

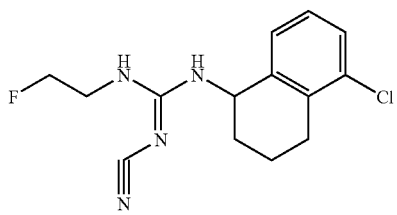

Synthesis of 1-(5-chloro-1,2,3,4-tetrahydro-naphthalen-1-yl)-3-(2-fluoro-ethyl)-cyanoguanidine

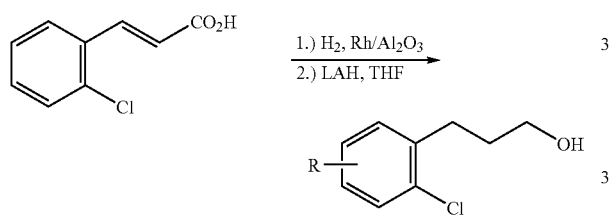

The desired starting 3-(2-chlorophenyl)propan-1-ol was prepared from the commercially available 3-(2-chlorophenyl)-acrylic acid using the protocol described in the scheme above. The title cyanoguanidine was thus obtained from this alcohol according to general procedure D. The intermediates 3-(2-chlorophenyl)propan-1-ol, 4-(2-chlorophenyl)butyronitrile, 5-chloro-3,4-dihydro-2H-naphthalen-1-one and 5-chloro-1,2,3,4-tetrahydro-naphthalen-1-ylamine were separated and characterized.

3-(2-Chloro-phenyl)-propan-1-ol[xii]: 3-(2-Chloro-phenyl)-acrylic acid (10.00 g, 55.00 mmol) in THF was mixed with Rh/Al$_2$O$_3$ (800 mg) and hydrogenated at 50 psi for 6 hours. The resulting mixture was filtered through a pad of celite and the filtrate was concentrated. The residue was dissolved in THF and cooled to 0° C. LAH (55.00 mL, 1.0 M in THF, 55.00 mmol) was added and the reaction mixture was stirred for 14 hours. The resulting mixture was quenched with NaOH and extracted with Et$_2$O (3×250 mL). The combined organic extracts were washed with H$_2$O (3×150 mL), brine (1×150 mL), dried over MgSO$_4$ and concentrated to give the title alcohol.

[xii] Baddar et al. *J. Chem. Soc.* 1959, 1027-1029.

4-(2-Chloro-phenyl)-butyronitrile[xiii]: The title compound was obtained from 3-(2-chloro-phenyl)-propan-1-ol (taken from the previous step without further purification), Et$_3$N (15.00 mL, 0.11 mol), MsCl (7.00 mL, 90.44 mmol) and KCN (7.02 g, 0.11 mol) according to the protocols as outlined in procedure D.

[xiii] Bunnett, J. F.; Skorcz, J. A. *J. Org. Chem.* 1962, 27, 3836-3843.

5-Chloro-3,4-dihydro-2H-naphthalen-1-one[14]: The title compound was obtained from 4-(2-chloro-phenyl)-butyronitrile (taken from the previous step without further purification), KOH (4.00 g, 71.29 mmol), SOCl$_2$ (4.00 mL, 54.84 mmol) and AlCl$_3$ (5.30 g, 39.75 mmol) according to the protocols as outlined in procedure D.

5-Chloro-1,2,3,4-tetrahydro-naphthalen-1-ylamine[xiv]:
The title compound was obtained from 5-Chloro-3,4-dihydro-2H-naphthalen-1-one (6.00 g, 33.30 mmol), NaBH$_3$CN (15.00 g, 0.24 mol) and NH$_4$OAc (77.00 g, 1.00 mol) according to the protocols as outlined in procedure B.

[xiv] Kuiban et al. *J. Gen. Chem. USSR (Engl. Transl.)* 1964, 34, 1592; *Zh. Obshch. Khim.* 1964, 34, 1581.

1-(5-Chloro-1,2,3,4-tetrahydro-naphthalen-1-yl)-3-(2-fluoro-ethyl)-cyanoguanidine: The title compound was obtained from 5-chloro-1,2,3,4-tetrahydro-naphthalen-1-ylamine (1.60 g, 8.80 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-dd$_6$) □ 1.49-2.14 (m, 4H), 2.7 (br s, 2H), 3.44-3.59 (m, 2H), 4.36-4.46 (m, 1H), 4.51-4.61 (m, 1H), 5.0 (br s, 1H), 7.15-7.24 (m, 2H), 7.27-7.38 (m, 3H). $^{13}$C NMR (75 MHz, DMSO-d$_6$) □ 20.0, 27.5, 29.5, 42.2 (d, J=20.7 Hz), 50.3, 82.8 (d, J=166.4 Hz), 118.5, 127.5, 127.7, 128.2, 133.9, 135.7, 140.3, 159.6.

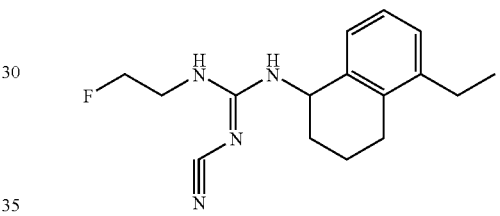

Synthesis of 1-(5-ethyl-1,2,3,4-tetrahydro-naphthalen-1-yl)-3-(2-fluoro-ethyl)-cyanoguanidine

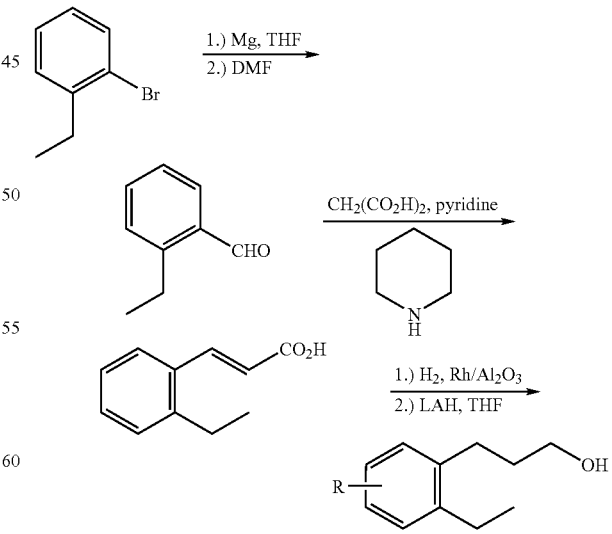

The desired starting 3-(2-ethylphenyl)propan-1-ol was prepared from the commercially available 1-bromo-2-ethylbenzene using the protocol described in the scheme above.

The title cyanoguanidine was thus obtained from this alcohol according to general procedure D. The intermediates 2-ethylbenzaldehyde, 3-(2-ethylphenyl)acrylic acid, 3-(2-ethylphenyl)propan-1-ol, 4-(2-ethylphenyl)butyronitrile, 5-ethyl-3,4-dihydro-2H-naphthalen-1-one and 5-ethyl-1,2,3,4-tetrahydro-naphthalen-1-ylamine were separated and characterized.

2-Ethyl-benzaldehyde[8]: 1-Bromo-2-ethyl-benzene (5.00 g, 27.00 mmol), Mg (4.00 g, 164.54 mmol) and a catalytic amount of $I_2$ in THF were refluxed for 2 hours. The reaction mixture was cooled to 0° C., DMF (10.00 mL, 129.17 mmol) was added. The resulting reaction mixture was stirred for 30 minutes, then was quenched with 10% HCl. The resulting solution was extracted with $Et_2O$ (3×200 mL) and the combined organic extracts were washed with $H_2O$ (2×200 mL) and brine (1×200 mL), then dried over $MgSO_4$ and concentrated to give the desired title benzaldehyde.

3-(2-Ethyl-phenyl)-acrylic acid[9]: 2-Ethyl-benzaldehyde (18.40 g, 0.14 mol) and malonic acid (28.00 g, 0.27 mol) were mixed in pyridine, then 10.00 mL of piperidine was added. The resulting mixture was slowly refluxed for 3 hours. After cooling to room temperature, the reaction mixture was quenched into cold water, acidified to pH<1 and the resulting solid was filtered, washed with water and dried under vacuum to give the desired title acid.

3-(2-Ethyl-phenyl)-propan-1-ol: 3-(2-Ethyl-phenyl)-acrylic acid (17.00 g, 96.60 mmol) in THF was mixed with Pd/C (1.50 g) and hydrogenated at 50 psi for 6 hours. The resulting mixture was filtered through a pad of celite and the filtrate was concentrated. The residue was dissolved in THF and cooled to 0° C. LAH (100.00 mL, 1.0 M in THF, 0.10 mol) was added and the reaction mixture was stirred for 14 hours. The resulting mixture was quenched with NaOH and extracted with $Et_2O$ (3×250 mL). The combined organic extracts were washed with $H_2O$ (3×150 mL) and brine (1×150 mL), then dried over $MgSO_4$ and concentrated to give the title alcohol.

4-(2-Ethyl-phenyl)-butyronitrile: The title compound was obtained from 3-(2-ethyl-phenyl)-propan-1-ol (taken from the previous step without further purification), $Et_3N$ (13.00 mL, 93.27 mmol), MsCl (5.50 mL, 71.06 mmol) and KCN (6.50 g, 99.82 mmol) according to the protocols as outlined in general procedure D.

5-Ethyl-3,4-dihydro-2H-naphthalen-1-one[xv]: The title compound was obtained from of 3-(2-ethyl-phenyl)-propionitrile (taken from the previous step without further purification), KOH (4.00 g, 71.29 mmol), $SOCl_2$ (4.00 mL, 54.84 mmol) and $AlCl_3$ (5.40 g, 40.50 mmol) according to the protocols as outlined in general procedure D.

[xv] Burnham, J. W. et al. *J. Org. Chem.* 1974, 39, 1416-1420.

5-Ethyl-1,2,3,4-tetrahydro-naphthalen-1-ylamine: The title compound was obtained from 5-ethyl-3,4-dihydro-2H-naphthalen-1-one (4.50 g, 25.90 mmol), $NaBH_3CN$ (11.40 g, 0.18 mol) and $NH_4OAc$ (60.00 g, 0.78 mol) according to the protocols as outlined in general procedure B.

1-(5-Ethyl-1,2,3,4-tetrahydro-naphthalen-1-yl)-3-(2-fluoro-ethyl)-cyanoguanidine: The title compound was obtained from 5-ethyl-1,2,3,4-tetrahydro-naphthalen-1-ylamine (1.60 g, 9.20 mmol) and 1-(2-fluoro-ethyl)-2-phenyl-3-cyanoisourea (1.00 g, 4.83 mmol) according to the protocols as outlined in general procedure A above. Spectroscopic data: $^1$H NMR (300 MHz, DMSO-$d_6$) □ 1.2 (t, J=7.3 Hz, 3H), 1.68-1.80 (m, 2H), 1.84-1.95 (m, 2H), 2.5 (q, J=7.6 Hz, 2H), 2.7 (t, J=5.9, 5.3 Hz, 2H), 3.42-3.57 (m, 2H), 4.4 (t, J=5.0 Hz, 1H), 4.5 (t, J=5.0 Hz, 1H), 4.90-5.04 (m, 1H), 7.01-7.13 (m, 3H), 7.15-7.24 (m, 2H). $^{13}$C NMR (75 MHz, DMSO-$d_6$) □ 14.9, 20.6, 25.8, 26.0, 30.0, 42.2 (d, J=20.7 Hz), 50.8, 82.8 (d, J=166.4 Hz), 118.5, 126.2, 126.3, 127.2, 135.7, 137.6, 142.3, 159.6.

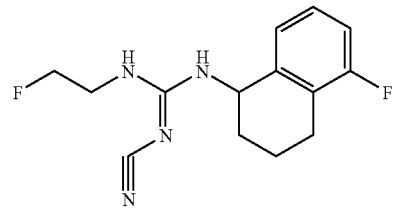

Synthesis of 1-(2-fluoro-ethyl)-3-(5-fluoro-1,2,3,4-tetrahydro-naphthalen-1-yl)-cyanoguanidine

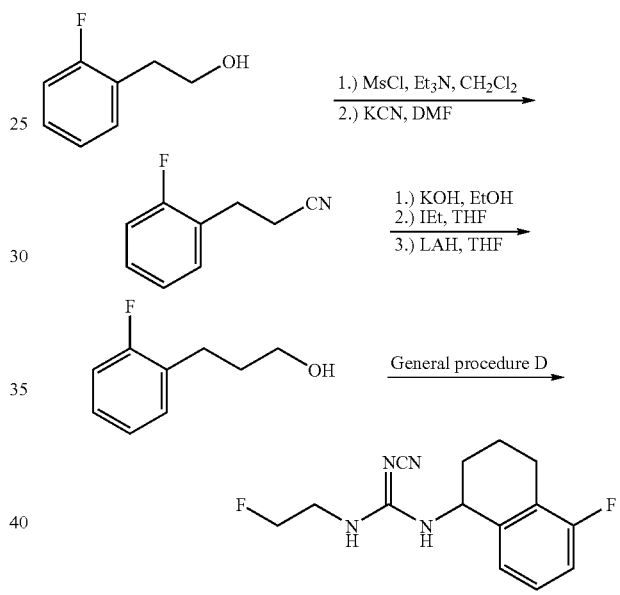

3-(2-Fluoro-phenyl)-propionitrile: To a solution of 2-(2-fluoro-phenyl)-ethanol (10.00 g, 71.50 mmol) in $CH_2Cl_2$ at 0° C. was added $Et_3N$ (20.00 mL, 0.14 mol) followed by MsCl (19.00 mL, 0.25 mol). The resulting mixture was stirred for 1 hour, then washed with $H_2O$ (3×100 mL) and brine (1×150 mL), dried over $MgSO_4$ and concentrated. The residue was dissolved in DMF and KCN (9.30 g, 0.14 mol) was added. The resulting mixture was stirred at 75° C. for 14 hours. After cooling to room temperature, the reaction mixture was quenched into water and extracted with $Et_2O$ (3×300 mL). The combined organic extracts were washed with $H_2O$ (2×200 mL), brine (1×200 mL), dried over $MgSO_4$ and concentrated to give the title compound.

3-(2-Fluoro-phenyl)-propan-1-ol: 3-(2-Fluoro-phenyl)-propionitrile (taken from the previous step without further purification) was dissolved in ethanol and KOH (8.00 g, 0.14 mol) was added. The resulting mixture was refluxed for 14 hours. After cooling to room temperature, the reaction mixture was diluted with water and washed with $Et_2O$ (2×150 mL). The aqueous layer was acidified with concentrated HCl, then extracted with $Et_2O$ (3×300 mL). The combined organic phases were washed with $H_2O$ (2×200 mL), and brine (1×200 mL), then dried over $MgSO_4$ and concentrated to give the desired (3-chloro-2-fluoro-phenyl)-acetic acid. The acid was then dissolved in THF and iodoethane (12.00 mL, 0.15 mol) was added. The resulting mixture was refluxed for 2 hours. After cooling to room temperature, the reaction mixture was extracted with Et$_2$O (3×300 mL) and the combined organic extracts were washed with H$_2$O (2×200 mL) and brine (1×200 mL), then dried over MgSO$_4$ and concentrated to give the desired 3-(2-fluoro-phenyl)-propionic acid ethyl ester. This ethyl ester was then dissolved in THF and cooled to 0° C. LAH (72.00 mL, 1.0 M in THF, 72.00 mmol) was added. The resulting reaction mixture was stirred for 14 hours, then quenched with NaOH. The resulting mixture was extracted with Et$_2$O (3×250 mL) and the combined organic extracts were washed with H$_2$O (3×150 mL) and brine (1×150 mL), then dried over MgSO$_4$ and concentrated to give the desired title alcohol.

4-(2-Fluoro-phenyl)-butyronitrile: The title compound was obtained from 3-(2-fluoro-phenyl)-propan-1-ol (taken from the previous step without further purification), Et$_3$N (20.00 mL, 143.63 mmol), MsCl (9.00 mL, 0.12 mol) and KCN (9.30 g, 0.14 mol) according to the protocols as outlined in general procedure D.

5-Fluoro-3,4-dihydro-2H-naphthalen-1-one: The title compound was obtained from 3-(2-Fluoro-phenyl)-butyronitrile (taken from the previous step without further purification), KOH (8.00 g, 0.14 mol), SOCl$_2$ (7.00 mL, 95.97 mmol) and AlCl$_3$ (9.50 g, 71.25 mmol) according to general procedure D.

5-Fluoro-1,2,3,4-tetrahydro-naphthalen-1-ylamine: The title amine was obtained from 5-fluoro-3,4-dihydro-2H-naphthalen-1-one (4.50 g, 27.40 mmol), NaBH$_3$CN (12.00 g, 0.19 mol) and NH$_4$OAc (63.40 g, 0.82 mol) according to the protocols as outlined in general procedure D.

1-(2-Fluoro-ethyl)-3-(5-fluoro-1,2,3,4-tetrahydro-naphthalen-1-yl)-cyanoguanidine: The title compound was obtained from 5-fluoro-1,2,3,4-tetrahydro-naphthalen-1-ylamine (1.50 g, 9.10 mmole) and 1-(2-fluoro-ethyl)-2-phenyl-3-cyanoisourea (1.00 g, 4.83 mmol) in CH$_3$CN according to the protocols as outlined in general procedure A above. Spectroscopic data: $^1$H NMR (300 MHz, DMSO-d$_6$) δ 1.68-1.82 (m, 2H), 1.85-1.96 (m, 2H), 2.58-2.73 (m, 2H), 3.42-3.57 (m, 2H), 4.4 (t, J=5.0 Hz, 1H), 4.5 (t, J=4.7, 4.1 Hz, 1H), 4.92-5.05 (m, 1H), 7.1 (t, J=9.1, 7.9 Hz, 2H), 7.18-7.34 (m, 3H). $^{13}$C NMR (75 MHz, DMSO-d$_6$) δ 19.8, 22.1, 29.8, 42.2 (d, J=20.7 Hz), 50.0, 82.8 (d, J=166.4 Hz), 113.6 (d, J=21.8 Hz), 118.4, 124.2, 125.4 (d, J=18.4 Hz), 127.5 (d, J=9.2 Hz), 140.4 (d, J=4.6 Hz), 160.6 (d, J=242.1 Hz), 159.7.

General Procedure E for the Synthesis of Fluoroethyl Indan Cyanoguanidines

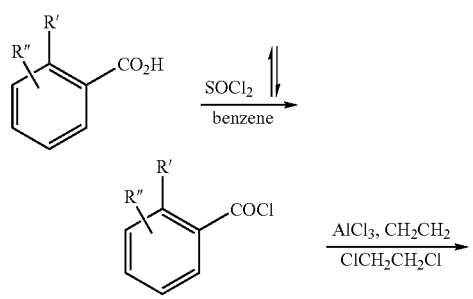

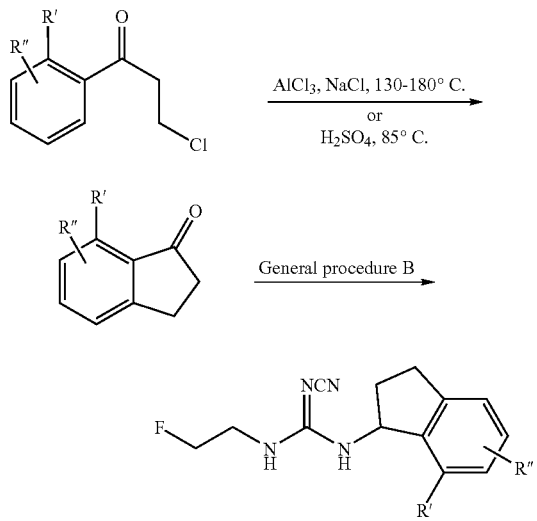

A solution of SOCl$_2$ (1.5 eq) and substituted benzoic acid in benzene was refluxed until no more gas evolution was observed. After cooling to room temperature the reaction mixture was concentrated. The concentrate was taken up in dichloroethane and added to a suspension of AlCl$_3$ (1.0 eq) in dichloroethane at 10-20° C. Ethylene was bubbled for 4 hours, then the resulting mixture was stirred for 14 hours and quenched into 4 N HCl. The resulting layers were separated and the aqueous layer was extracted with Et$_2$O (3×250 mL). The combined organic extracts were washed with H$_2$O (3×100 mL), saturated NaHCO$_3$ (3×100 mL) and brine (1×100 mL), then dried over MgSO$_4$ and concentrated.

For halogen-containing analogs, the following cyclization procedure was followed: The concentrate containing crude halo substituted phenylpropan-1-one was added to a slurry of AlCl$_3$ (10.0 eq) and NaCl (6.0 eq) at 130° C. The resulting mixture was stirred at 180° C. for 2 hours, then cooled to room temperature and slowly quenched with ice, followed by concentrated HCl. The resulting mixture was extracted with CH$_2$Cl$_2$ (3×300 mL) and the combined extracts were concentrated and purified by column chromatography using hexane:EtOAc (4:1) as eluant to give the desired pure indanone.

For alkyl and halogen-containing analogs, the following cyclization procedure was followed: Concentrated sulfuric acid was added to the concentrate containing crude halo and alkyl substituted phenylpropan-1-one and the mixture was stirred at 85° C. for 1 hour. After cooling to room temperature, the reaction mixture was quenched into ice-water. The resulting mixture was extracted with Et$_2$O (3×200 mL) and the combined extracts were washed with H$_2$O (3×200 mL), saturated NaHCO$_3$ (3×200 mL) and brine (1×100 mL), then dried over MgSO$_4$ and concentrated. The pure indanone was obtained after column chromatography using hexane:EtOAc (4:1) as eluant. The desired final cyanoguanidine was thus obtained from this indanone according to the protocols described in general procedure B.

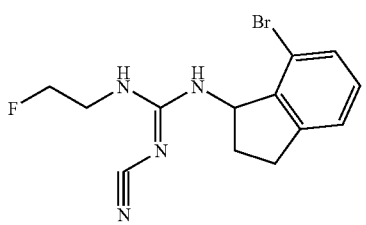

Synthesis of 1-(7-bromo-indan-1-yl)-3-(2-fluoro-ethyl)-cyanoguanidine

The title cyanoguanidine was obtained from the commercially available 2-bromobenzoic acid according to general procedure E. The intermediates 7-bromo-1-one and 7-bromoindan-1-ylamine were separated and characterized.

7-Bromo-1-indanone: 9.68 g (31%) of the title amine was obtained from 2-bromo-benzoic acid (30.00 g, 0.15 mol), SOCl$_2$ (16.50 mL, 0.23 mol), AlCl$_3$ (20.00 g, 0.15 mol), an additional AlCl$_3$ (200.00 g, 1.50 mol) and NaCl (52.30 g, 0.89 mol) according to the protocols as outlined in general procedure E. Spectroscopic data: $^1$H NMR (300 MHz, CDCl$_3$) ☐ 2.69-2.79 (m, 2H), 3.04-3.14 (m, 2H), 7.35-7.45 (m, 2H), 7.49-7.55 (m, 1H).

7-Bromo-indan-1-ylamine: 4.84 g of The crude amine (used in the next step without further purification) was obtained from 7-bromo-1-indanone (8.00 g, 38.00 mmol), NaBH$_3$CN (16.70 g, 0.27 mol) and NH$_4$OAc (88.00 g, 1.14 mol) according to the protocols as outlined in general procedure B.

1-(7-Bromo-indan-1-yl)-3-(2-fluoro-ethyl)-cyanoguanidine: The title compound was obtained from 7-bromo-indan-1-ylamine (2.42 g, 11.40 mmol) and 1-(2-fluoro-ethyl)-2-phenyl-3-cyanoisourea (1.20 g, 5.79 mmol) according to the protocols as outlined in general procedure A. Spectroscopic data: $^1$H NMR (300 MHz, DMSO-d$_6$) ☐ 1.86-1.99 (m, 1H), 2.33-2.46 (m, 1H), 2.78-2.91 (m, 1H), 3.05-3.19 (m, 1H), 3.39-3.55 (m, 2H), 4.4 (t, 1H, J=5.3 Hz), 4.5 (t, 1H, J=5.0 Hz), 5.24-5.36 (m, 1H), 7.2 (t, 2H, J=7.6 Hz), 7.27-7.36 (m, 2H), 7.4 (d, 1H, J=7.9 Hz). $^{13}$C NMR (75 MHz, DMSO-d$_6$) ☐ 31.2, 33.3, 42.1 (d, J=20.7 Hz), 58.1, 82.6 (d, J=166.4 Hz), 118.4, 120.5, 124.7, 130.7, 130.9, 141.7, 147.9, 159.3.

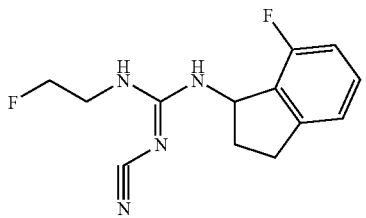

Synthesis of 2-(2-fluoro-ethyl)-3-(7-fluoro-indan-1-yl)-cyanoguanidine

The title cyanoguanidine was obtained from the commercially available 2-fluorobenzoic acid according to general procedure E. The intermediates 7-fluoro-1-one and 7-fluoroindan-1-ylamine were separated and characterized.

7-Fluoro-1-indanone: 6.85 g (32%) of the title indanone was obtained from 2-fluoro-benzoic acid (20.00 g, 0.14 mol), SOCl$_2$ (15.60 mL, 0.21 mol), AlCl$_3$ (19.00 g, 0.14 mol), an additional AlCl$_3$ (285.50 g, 2.14 mol) and NaCl (75.10 g, 1.29 mol) according to the protocols as outlined in general procedure E. Spectroscopic data: $^1$H NMR (300 MHz, CDCl$_3$) ☐ 2.67-2.80 (m, 2H), 3.2 (t, 2H, J=5.9 Hz), 7.0 (t, 1H, J=8.5 Hz), 7.3 (d, 1H, J=7.6 Hz), 7.6 (m, 1H).

7-Fluoro-indan-1-ylamine: The title compound was obtained from 7-fluoro-1-indanone (5.82 g, 39.00 mmol), NaBH$_3$CN (17.10 g, 0.27 mol) and NH$_4$OAc (90.00 g, 1.17 mol) according to the protocols as outlined in general procedure B. Spectroscopic data: $^1$H NMR (300 MHz, CDCl$_3$) ☐ 1.69-2.25 (m, 3H), 2.40-2.54 (m, 1H), 2.77-2.92 (m, 1H), 3.00-3.15 (m, 1H), 4.62 (t, J=7.04, 6.16 Hz, 1H), 6.77-6.90 (m, 1H), 7.00 (t, J=8.21 Hz, 1H), 7.10-7.22 (m, 1H).

1-(2-Fluoro-ethyl)-3-(7-fluoro-indan-1-yl)-cyanoguanidine: The title compound was obtained from A solution of 7-fluoro-indan-1-ylamine (2.43 g, 16.10 mmol) and 1-(2-fluoro-ethyl)-2-phenyl-3-cyanoisourea (1.70 g, 8.20 mmol) according to the protocols as outlined in general procedure A. Spectroscopic data: $^1$H NMR (300 MHz, DMSO-d$_6$) ☐ 1.88-2.01 (m, 1H), 2.38-2.51 (m, 1H), 2.75-2.87 (m, 1H), 2.97-3.10 (m, 1H), 3.40-3.55 (m, 2H), 4.4 (t, 1H, J=5.0 Hz), 4.5 (t, 1H, J=5.3 Hz), 5.5 (q, 1H, J=7.6 Hz), 7.0 (t, 1H, J=9.1 Hz), 7.1 (d, 1H, J=7.3 Hz), 7.19-7.34 (m, 2H), 7.4 (d, 1H, J=8.5 Hz). $^{13}$C NMR (75 MHz, DMSO-d$_6$) ☐ ☐ 0.8, 33.9, 42.2 (d, J=21.8 Hz), 54.9, 82.5 (d, J=166.4 Hz), 113.7 (d, J=20.7 Hz), 118.3, 121.4 (d, J=3.4 Hz), 129.0 (d, J=14.9 Hz), 131.0 (d, J=8.0 Hz), 148.0 (d, J=4.6 Hz), 159.3, 160.0 (d, J=246H).

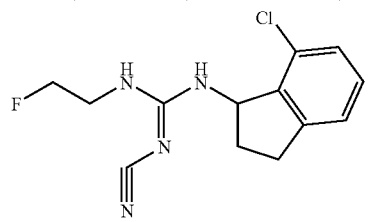

Synthesis of 1-(7-chloro-indan-1-yl)-3-(2-fluoro-ethyl)-cyanoguanidine

The title cyanoguanidine was obtained from the commercially available 2-chlorobenzoic acid according to general procedure E. The intermediates 7-chloro-1-one and 7-chloroindan-1-ylamine were separated and characterized.

7-Chloro-1-indanone: 4.13 g (31%) of the title indanone was obtained from 2-chloro-benzoic acid (10.0 g, 64.00 mmol), SOCl$_2$ (7.00 mL, 95.97 mmol), AlCl$_3$ (8.50 g, 63.75 mmol), an additional AlCl$_3$ (85.20 g, 0.64 mol) and NaCl (22.40 g, 0.38 mol) according to the protocols as outlined in general procedure E. Spectroscopic data: $^1$H NMR (300 MHz, CDCl$_3$) ☐ 2.65-2.75 (m, 2H), 3.1 (t, 2H, J=6.7, 5.6 Hz), 7.3 (d, 1H, J=7.6 Hz), 7.4 (d, 1H, J=7.6 Hz), 7.5 (t, 1H, J=7.6 Hz).

7-Chloro-indan-1-ylamine: 1.00 g of the crude title amine (used in the next step without further purification) was obtained from 7-chloro-1-indanone (4.13 g, 25.00 mmol), NaBH$_3$CN (11.00 g, 0.17 mol) and NH$_4$OAc (57.4 g, 0.74 mol) according to the protocols as outlined in general procedure B. Spectroscopic data: $^1$H NMR (300 MHz, CDCl$_3$) ☐ 1.7 (br s, 2H), 1.82-1.92 (m, 1H), 2.37-2.51 (m, 1H), 2.79-2.94 (m, 1H), 3.07-3.19 (m, 1H), 4.48-4.59 (m, 1H), 7.07-7.16 (m, 3H).

1-(7-Chloro-indan-1-yl)-3-(2-fluoro-ethyl)-cyanoguanidine: The title compound was obtained from 7-chloro-indan-1-ylamine (1.00 g, 6.00 mmol) and 1-(2-fluoro-ethyl)-2-phenyl-3-cyanoisourea (660 mg, 3.19 mmol) according to the protocols as outlined in general procedure A. Spectroscopic data: $^1$H NMR (300 MHz, DMSO-d$_6$) ☐ 1.86-1.98 (m, 1H), 2.35-2.47 (m, 1H), 2.76-2.89 (m, 1H), 3.03-3.16 (m, 1H), 3.39-3.55 (m, 2H), 4.4 (t, 1H, J=5.3 Hz), 4.5 (t, 1H, J=5.0 Hz), 5.34-5.46 (m, 1H), 7.19-7.33 (m, 4H), 7.4 (d, 1H, J=8.5 Hz). $^{13}$C NMR (75 MHz, DMSO-d$_6$) ☐ 131.0, 33.4, 42.2 (d, J=20.7 Hz), 56.7, 82.5 (d, J=166.4 Hz), 118.4, 124.2, 127.7, 130.7, 131.2, 139.9, 147.7, 159.3.

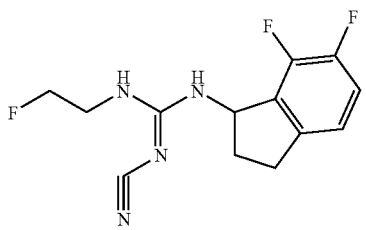

Synthesis of N-(6,7-difluoro-indan-1-yl)-N'-(2-fluoro-ethyl)-cyanoguanidine

The title cyanoguanidine was obtained from the commercially available 2-3-difluorobenzoic acid according to general procedure E. The intermediates 6,7-difluoro-1-one and 6,7-difluoroindan-1-ylamine were separated and characterized.

Synthesis of 6,7-difluoro-1-indanone: A solution of 2,3-difluoro-benzoic acid (10.30 g, 65.14 mmol), SOCl$_2$ (7.20 mL, 98.71 mmol), AlCl$_3$ (8.70 g, 65.25 mmol), an additional AlCl$_3$ (87.0 g, 0.65 mol) and NaCl (23.00 g, 0.39 mol) was reacted according to the protocols as outlined in general procedure E to give 6.00 g (55%) of the title compound. Spectroscopic data: $^1$H NMR (300 MHz, CDCl$_3$) ☐ 2.73-2.80 (m, 2H), 3.09-3.16 (m, 2H), 7.11-7.23 (m, 1H), 7.35-7.46 (m, 1H).

6,7-Difluoro-indan-1-ylamine: A solution of 6,7-difluoro-1-indanone (6.00 g, 35.70 mmol), NaBH$_3$CN (15.70 g, 0.25 mol) and NH$_4$OAc (82.60 g, 1.07 mol) in isopropanol was reacted according to the protocols as outlined in general procedure B to give 3.00 g of the crude title compound, which was used in the next step without further purification. Spectroscopic data: $^1$H NMR (300 MHz, CDCl$_3$) ☐ 1.7 (br s, 2H), 1.78-1.90 (m, 1H), 2.44-2.57 (m, 1H), 2.72-2.87 (m, 1H), 2.95-3.09 (m, 1H), 4.7 (t, 1H, J=6.7 Hz), 6.86-7.00 (m, 2H).

1-(6,7-Difluoro-indan-1-yl)-3-(2-fluoro-ethyl)-cyanoguanidine: The title compound was obtained 6,7-difluoro-indan-1-ylamine (1.50 g, 9.00 mmol) and 1-(2-fluoro-ethyl)-2-phenyl-3-cyanoisourea (930 mg, 4.45 mmol) according to the protocols as outlined in general procedure A. Spectroscopic data: $^1$H NMR (300 MHz, DMSO-d$_6$) ☐ 1.92-2.05 (m, 1H), 2.41-2.54 (m, 1H), 2.71-2.85 (m, 1H), 2.92-3.05 (m, 1H), 3.40-3.55 (m, 2H), 4.4 (t, 1H, J=5.6 Hz), 4.5 (t, 1H, J=5.0 Hz), 5.5 (q, 1H, J=7.3 Hz), 7.02-7.12 (m, 1H), 7.22-7.35 (m, 2H), 7.5 (d, 1H, J=8.2 Hz). $^{13}$C NMR (75 MHz, DMSO-d$_6$) ☐ 30.3, 34.6, 42.2 (d, J=20.7 Hz), 55.3, 82.5 (d, J=166.4 Hz), 117.8 (d, J=18.4 Hz), 118.2, 121.2 (dd, J=6.9, 3.4 Hz), 131.6 (d, J=10.3 Hz), 142.5, 147.3 (dd, J=248.2, 11.5 Hz), 149.0 (dd, J=242, 13.8 Hz), 159.4.

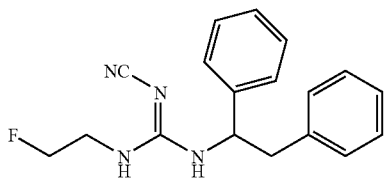

Synthesis of 1-(1,2-diphenyl-ethyl)3'-(2-fluoro-ethyl)-cyanoguanidine

The title compound was obtained from the commercially available 1,2-diphenyl-ethylamine according to general procedure A described above.

1-(1,2-Diphenyl-ethyl)3'-(2-fluoro-ethyl)-cyanoguanidine: The title compound was obtained from 1,2-diphenyl-ethylamine (586 mg, 2.97 mmol) and 1-(2-fluoro-ethyl)-2-phenyl-3-cyanoisourea (560 mg, 2.70 mmol) according to the protocols as outlined in general procedure A. Spectroscopic data: $^1$H NMR (300 MHz, CDCl$_3$) ☐ ppm 3.11 (d, J=7.04 Hz, 2H) 3.29-3.45 (m, 2H) 4.25 (ddd, J=8.94, 4.40, 4.25 Hz, 1H) 4.34-4.47 (m, 1H) 4.68 (q, J=6.64 Hz, 1H) 4.94 (br s, 1H) 5.86 (d, J=4.40 Hz, 1H) 7.08 (d, J=7.04 Hz, 2H) 7.22 (d, J=6.74 Hz, 2H) 7.26-7.30 (m, 3H) 7.35 (t, J=7.33 Hz, 3H).

The invention claimed is:

1. A compound having a formula

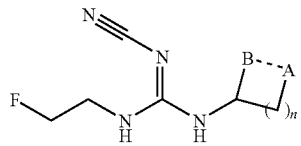

wherein a dashed line indicates the presence or absence of a bond;

n is 0 or 1;

A is substituted or unsubstituted phenyl;

B is alkyl having 1, 2, 3, or 4 carbon atoms; or

B is H or substituted or unsubstituted phenyl and the dashed line is not a covalent bond.

2. The compound of claim 1 wherein A is phenyl substituted with 0, 1, 2, 3, or 4 substituents, wherein the substituents are independently alkyl having from 1 to 4 carbon atoms or a halogen.

3. The compound of claim 2 wherein the substituents are independently methyl, ethyl, F, Cl, or Br.

4. The compound of claim 1 wherein A is unsubstituted phenyl.

5. The compound of claim 1 having a formula

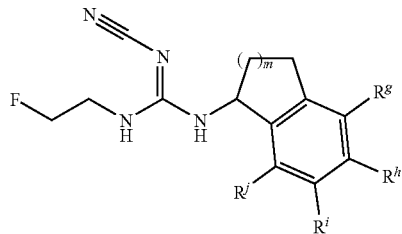

wherein m is 0 or 1; and

R$^g$, R$^h$, R$^i$, and R$^j$ are independently H, alkyl having from 1 to 6 carbon atoms, halogen, CN, CH$_2$CN, amine having from 1 to 6 carbon atoms, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

6. The compound of claim 5 having a formula

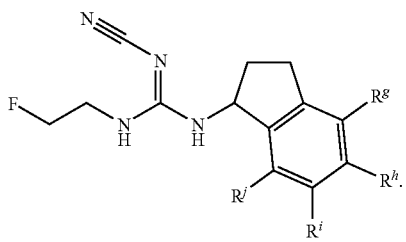

7. The compound of claim 1 having a formula

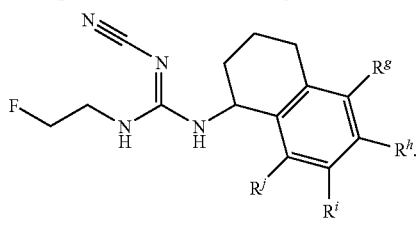

8. The compound of claim 1 having a formula

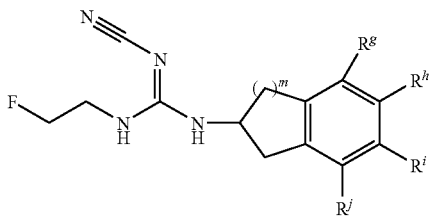

wherein m is 0 or 1; and $R^g$, $R^h$, $R^i$, and $R^j$ are independently H, alkyl having from 1 to 6 carbon atoms, halogen, CN, CH$_2$CN, amine having from 1 to 6 carbon atoms, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

9. The compound of claim 8 having a formula

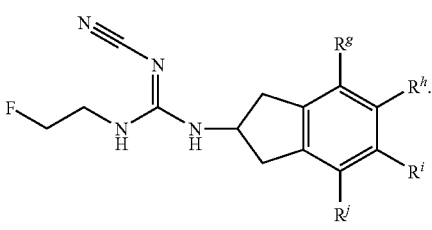

10. The compound of claim 8 having a formula

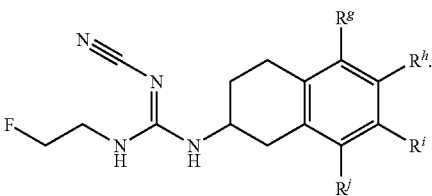

11. The compound of claim 1 having a formula

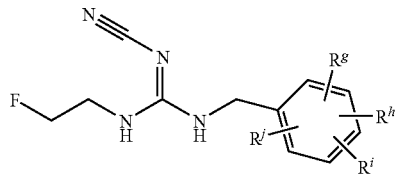

wherein $R^g$, $R^h$, $R^i$, and $R^j$ are independently H, alkyl having from 1 to 6 carbon atoms, halogen, CN, CH$_2$CN, amine having from 1 to 6 carbon atoms, hydroxyalkyl having from 1 to 6 carbon atoms, acyl having from 1 to 6 carbon atoms, O-alkyl having from 1 to 6 carbon atoms, amine substituents having from 0 to 6 carbon atoms, or S-alkyl having from 1 to 6 carbon atoms.

12. The compound of claim 1 having a formula

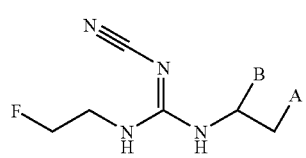

wherein A is substituted or unsubstituted phenyl; and

B is substituted or unsubstituted phenyl.

13. The compound of claim 1 selected from

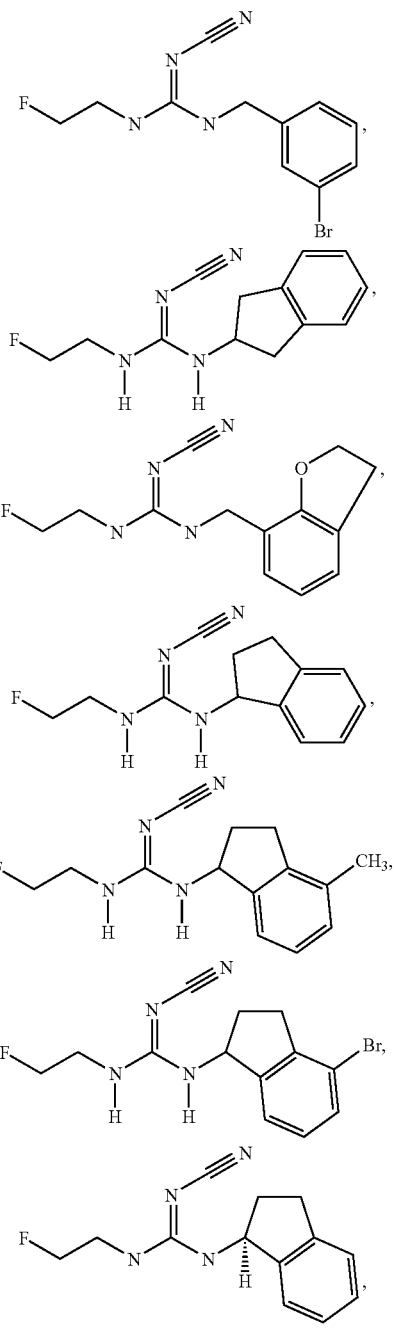

-continued
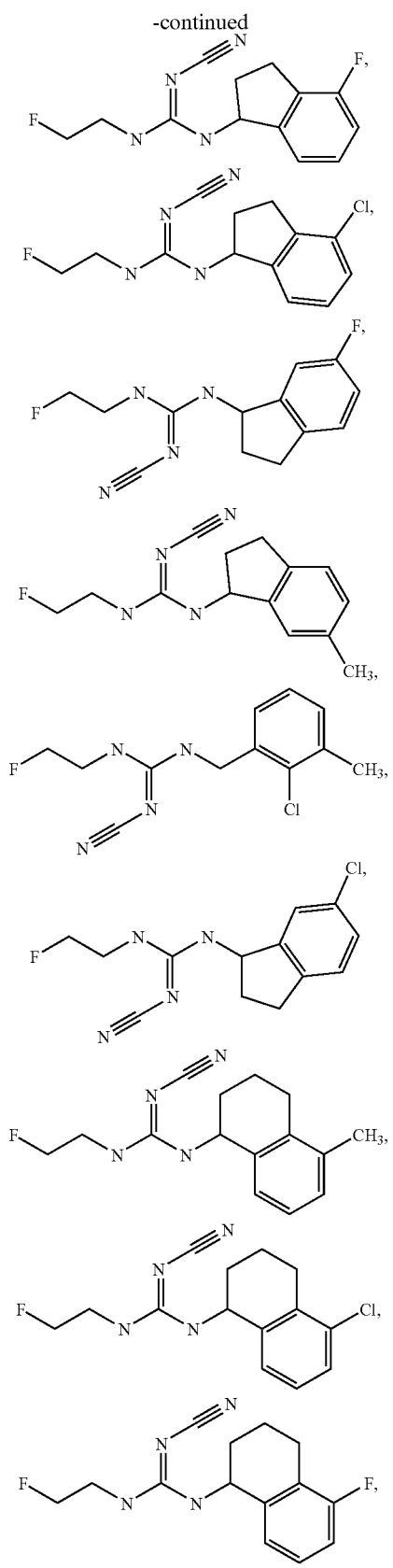
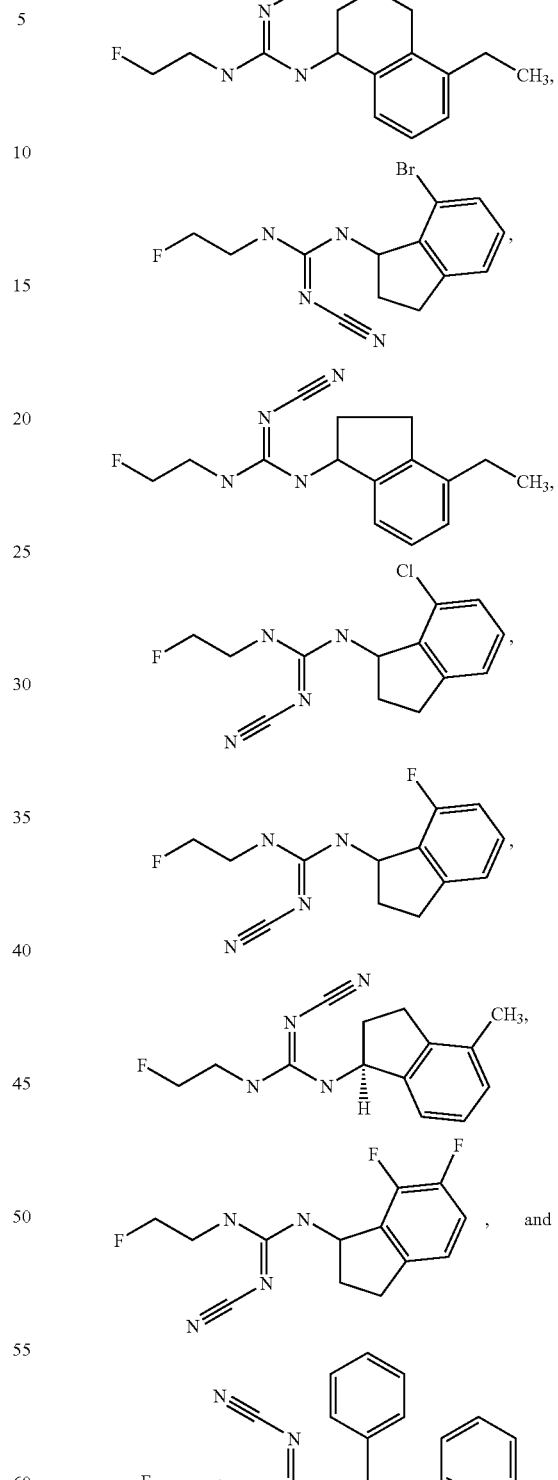
* * * * *